United States Patent [19]
von der Osten et al.

[11] Patent Number: 5,912,157
[45] Date of Patent: Jun. 15, 1999

[54] ALKALINE CELLULASES

[75] Inventors: Claus von der Osten, Lyngby; Martin Schülein, København Ø, both of Denmark

[73] Assignee: Novo Nordisk A/S, Bagsvaerd, Denmark

[21] Appl. No.: 08/709,979

[22] Filed: Sep. 9, 1996

Related U.S. Application Data

[63] Continuation-in-part of application No. PCT/DK95/00108, Mar. 8, 1995.

[30] Foreign Application Priority Data

Mar. 8, 1994 [DK] Denmark .................................. 0270/94
Mar. 30, 1994 [DK] Denmark .................................. 0365/94

[51] Int. Cl.$^6$ .............................. C12N 9/42; C11D 3/386; C12S 11/00
[52] U.S. Cl. ............................ 435/209; 435/267; 510/320
[58] Field of Search .................................. 435/209, 263; 510/320

[56] References Cited

U.S. PATENT DOCUMENTS

| | | | |
|---|---|---|---|
| 5,246,853 | 9/1993 | Clarkson et al. | 435/263 |
| 5,298,405 | 3/1994 | Nevalainen et al. | 435/204 |

FOREIGN PATENT DOCUMENTS

| | | |
|---|---|---|
| 0137280 | 4/1985 | European Pat. Off. . |
| 0495257 | 7/1992 | European Pat. Off. . |
| 0495258 | 7/1992 | European Pat. Off. . |
| 0540784 | 5/1993 | European Pat. Off. . |
| WO-85/04672 | 11/1985 | WIPO . |
| 91/17244 | 11/1991 | WIPO . |
| WO-91/17243 | 11/1991 | WIPO . |
| WO-91/17244 | 11/1991 | WIPO . |
| WO-93/05226 | 3/1993 | WIPO . |
| WO-94/07998 | 4/1994 | WIPO . |

OTHER PUBLICATIONS

Ong et al., Tibtech, vol. 7, pp. 239–243, (1989).
Van Arsdell et al, Biotechnology, vol. 5, pp. 60–64, (1987).
Sheppard et al., Gene, vol. 150, pp. 163–167, (1994).
Dialog Information Services, File 351, World Patent Index 81–95, Dialog accession No. 009814968, WPI accession No. 94–094824/12, Nippon Kami Pulp Kenkyusho KK: (1995).
Dialog Information Services, File 357, Derwent Biotechnology Abs, Dialog accession No. 071219, DBA accession No. 88–01567, Rikagaku–Res.Inst.: (1995).
Dialog Information Services, File 357, Derwent Biotechnology Abs, Dialog accession No. 086768, DBA accession No. 89–04759, Rao M. et al.: (1995).
Dialog Information Services, File 55, Biosis, Dialog accession No. 10066786, Biosis accession No. 95066786, Goto M. et al.: (1995).
Dialog Information Services, File 357, Derwent Biotechnology Abs, Dialog accession No. 125563, DBA accession No. 91–13205, Biely P. et al.: (1995).
National Library of Medicine, File Medline, NLM accession No. 94028932, Lao G.: (1993).
National Library of Medicine, File Medline, NLM accession No. 90197611, Bhat KM: (1990).
Dialog Information Services, File 55, Biosis, Dialog accession No. 4953447, Biosis accession No. 80080758, Okada G.: (1995).
Roy, S. K., et. al. (1990) J. Gen. Microbiol. 136, 1967–1971.
Oberson, J., et. al. (1992) Enzyme Microb. Technol. 14, 303–312.

*Primary Examiner*—Charles L. Patterson, Jr.
*Attorney, Agent, or Firm*—Steve T. Zelson, Esq.; Valeta Gregg, Esq.

[57] ABSTRACT

The present invention relates to cellulases derived from the strain *Myceliophthora thermophila* and variants thereof comprising a core and optionally a C-terminal link consisting of 10 amino acids at the most, especially cellulases having a substrate binding cleft of a depth of at least 12 Å, exhibit enhanced enzyme activity in the alkaline pH range while exerting a moderate cellulolytic action on the cellulosic substrate and are, for example, useful in detergent compositions, especially for soil removal or color clarification or preventing backstaining; in fabric softeners; for bio-polishing of textiles; for drainage improvement of paper pulp; for deinking of old paper; for plant degradation.

8 Claims, 2 Drawing Sheets

```
SEQUENCE            250         260         270         280         290         300       Res

EG1, Fusariu  SKPGLYGCTGDECG------SSGICDKAGCGWNHNRINVTDFYGRGKQYKVDSTRKFTV   268
EG1, Humicol  NKKGLYLCEGEECA------FEGVCDKNGCGWNNYRVNVTDYYGRGEEFKVNTLKPFTV   268
EG1, T.rees   TAT---ACDSAGCG------------FNPYGSGYKSYYGPGDTV--DTSKTFTI       249
CBH1, T.rees  TTVGQEICEGDGCGGTYSDNRYGGTCDPDGCDWNPYRLGNTSFYGPGSSFTLDTTKKLTV   290

SEQUENCE            310         320         330         340         350         360       Res

EG1, Fusariu  TSQFVANKQ---GDLIELHRHYIQDNKVIESAVVNISGPPKINFINDKYCAATGA----N   321
EG1, Humicol  VTQFLANRR---GKLEKIHRFYVQDGKVIESFYTNKEGVPYTNMIDDEFCEATGS----R   321
EG1, T.rees   ITQFNTDNGSPSGNLVSITRKYQQNGVDIPSA------QPGGDTISSCPSASA-----   296
CBH1, T.rees  VTQFETS------GAINRYYVQNGVTFQQPNAEL-GSYSGNELNDDYCTAEEAEFGGS   341

SEQUENCE            370         380         390         400         410         420       Res

EG1, Fusariu  EYMRLGGTKQMGDAMSRGMVLAMSVWWSEGDFMAWLDQG-----------VAGPCDATE   369
EG1, Humicol  KYMELGATQGMGEALTRGMVLAMSIWWDQGGNMEWLDHG-----------EAGPCAKGE   369
EG1, T.rees   ---YGGLATMGKALSSGMVLVFSIWNDNSQYMNWLDSG-----------NAGPCSSTE   340
CBH1, T.rees  SFSDKGGLTQFKKATSGGMVLVMSLWDDYYANMLWLDSTYPTNETSSTPGAVRGSCSTSS   401

SEQUENCE            430         440         450         460         470         480       Res

EG1, Fusariu  GDPKNIVKVQPNPEVTFSNIRIGEIGSTSSVKAPAYPGPHRL                    411
EG1, Humicol  GAPSNIVQVEPFPEVTYTNLRWGEIGSTYQEVQKPKPKPGHGPRSD                415
EG1, T.rees   GNPSNILANNPNTHVVFSNIRWGDIGSTTNSTAPPPPASSTTFST                 386
CBH1, T.rees  GVPAQVESQSPNAKVTFSNIKFGPIGSTGNPSG                             434
```

FIG. 1b

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 456 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Met Gly Arg Gly Ala Ala Phe Leu Gly Leu Ala Ser Leu Leu Val Gly
1               5                   10                  15

Ala Ala Lys Ala Gln Thr Pro Gly Glu Gly Glu Glu Val His Pro Gln
                20                  25                  30

Ile Thr Thr Tyr Arg Cys Thr Lys Ala Asp Gly Cys Glu Glu Lys Thr
            35                  40                  45

Asn Tyr Ile Val Leu Asp Ala Leu Ser His Pro Val His Gln Val Asp
        50                  55                  60

Asn Pro Tyr Asn Cys Gly Asp Trp Gly Gln Lys Pro Asn Glu Thr Ala
65                  70                  75                  80

Cys Pro Asp Leu Glu Ser Cys Ala Arg Asn Cys Ile Met Asp Pro Val
                85                  90                  95
```

Ser Asp Tyr Gly Arg His Gly Val Ser Thr Asp Gly Thr Ser Leu Arg
            100                 105                 110

Leu Lys Gln Leu Val Gly Gly Asn Val Val Ser Pro Arg Val Tyr Leu
            115                 120                 125

Leu Asp Glu Thr Lys Glu Arg Tyr Glu Met Leu Lys Leu Thr Gly Asn
            130                 135                 140

Glu Phe Thr Phe Asp Val Asp Ala Thr Lys Leu Pro Cys Gly Met Asn
145                 150                 155                 160

Ser Ala Leu Tyr Leu Ser Glu Met Asp Ala Thr Gly Ala Arg Ser Glu
            165                 170                 175

Leu Asn Pro Gly Gly Ala Thr Phe Gly Thr Gly Tyr Cys Asp Ala Gln
            180                 185                 190

Cys Tyr Val Thr Pro Phe Ile Asn Gly Leu Gly Asn Ile Glu Gly Lys
            195                 200                 205

Gly Ala Cys Cys Asn Glu Met Asp Ile Trp Glu Ala Asn Ala Arg Ala
            210                 215                 220

Gln His Ile Ala Pro His Pro Cys Ser Lys Ala Gly Pro Tyr Leu Cys
225                 230                 235                 240

Glu Gly Ala Glu Cys Glu Phe Asp Gly Val Cys Asp Lys Asn Gly Cys
            245                 250                 255

Ala Trp Asn Pro Tyr Arg Val Asn Val Thr Asp Tyr Tyr Gly Glu Gly
            260                 265                 270

Ala Glu Phe Arg Val Asp Thr Thr Arg Pro Phe Ser Val Val Thr Gln
            275                 280                 285

Phe Arg Ala Gly Gly Asp Ala Gly Gly Lys Leu Glu Ser Ile Tyr
            290                 295                 300

Arg Leu Phe Val Gln Asp Gly Arg Val Ile Glu Ser Tyr Val Val Asp
305                 310                 315                 320

Lys Pro Gly Leu Pro Pro Thr Arg Met Thr Asp Glu Phe Cys Ala
            325                 330                 335

Ala Thr Gly Ala Ala Arg Phe Thr Glu Leu Gly Ala Met Glu Ala Met
            340                 345                 350

Gly Asp Ala Leu Thr Arg Gly Met Val Leu Ala Leu Ser Ile Trp Trp
            355                 360                 365

Ser Glu Gly Asp Asn Met Asn Trp Leu Asp Ser Gly Glu Ala Gly Pro
            370                 375                 380

Cys Asp Pro Asp Glu Gly Asn Pro Ser Asn Ile Ile Arg Val Gln Pro
385                 390                 395                 400

Asp Pro Glu Val Val Phe Ser Asn Leu Arg Trp Gly Glu Ile Gly Ser
            405                 410                 415

Thr Tyr Glu Ser Ala Val Asp Gly Pro Val Gly Lys Gly Lys Gly Lys
            420                 425                 430

Gly Lys Gly Lys Ala Pro Ala Gly Asp Gly Asn Gly Lys Glu Lys Ser
            435                 440                 445

Asn Gly Lys Arg Phe Arg Phe
450                 455

(2) INFORMATION FOR SEQ ID NO:2:

(i) SEQUENCE CHARACTERISTICS:
        (A) LENGTH: 1560 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

```
TTCCCCCACG AGGAATTGAC AAAAGAAAAA GAAAAAGACA AGACTCTCGA GAACGATGGG    60
TCGCGGCGCT GCTTTCCTAG GCCTCGCCTC GCTCCTCGTG GGCGCGGCCA AGGCCCAGAC   120
GCCCGGCGAG GGCGAGGAGG TGCACCCGCA GATCACGACG TACCGCTGCA CCAAGGCGGA   180
CGGGTGCGAG GAGAAGACCA ACTACATCGT GCTGGACGCC CTATCGCACC CGGTCCACCA   240
GGTCGACAAC CCGTACAACT GCGGCGACTG GGGCCAGAAG CCCAACGAGA CGGCCTGCCC   300
GGACCTCGAG TCGTGCGCCA GGAACTGCAT CATGGACCCG GTCTCGGACT ACGGCCGGCA   360
CGGTGTCTCG ACCGACGGCA CCTCGCTGCG CCTCAAGCAG CTAGTCGGCG CAACGTCGT    420
CAGCCCGCGC GTCTACCTGC TCGACGAGAC CAAGGAGCGC TACGAGATGC TCAAGCTGAC   480
CGGCAACGAG TTCACCTTTG ACGTCGACGC CACCAAGCTG CCCTGCGGCA TGAACAGCGC   540
CCTCTACCTC TCCGAGATGG ACGCCACCGG CGCCCGGAGC GAGCTCAACC CGGGCGGCGC   600
CACCTTTGGC ACCGGCTACT GCGACGCCCA GTGCTACGTC ACCCCCTTCA TCAACGGCCT   660
CGGCAACATC GAGGGCAAGG GCGCGTGCTG CAACGAGATG GATATCTGGG AGGCCAACGC   720
GCGGGCGCAG CACATCGCGC CGCACCCGTG CAGCAAGGCG GGGCCGTACC TGTGCGAGGG   780
CGCCGAGTGC GAGTTCGACG GCGTGTGCGA CAAGAACGGC TGCGCCTGGA ACCCGTACCG   840
GGTCAACGTG ACGGACTACT ACGGCGAGGG CGCCGAGTTC AGGGTGGACA CGACCCGGCC   900
CTTCTCGGTC GTCACGCAGT TCCGCGCCGG CGGCGACGCG GGGGCGGCA AGCTCGAGAG    960
CATCTACCGG CTCTTCGTCC AGGACGGCAG GGTGATTGAG TCGTACGTCG TCGACAAGCC  1020
CGGCCTGCCC CCGACGGACC GCATGACGGA CGAGTTCTGC GCCGCCACCG GCGCCGCCCG  1080
CTTCACGGAG CTCGGCGCCA TGGAGGCCAT GGGCGACGCC CTGACGCGCG GCATGGTCCT  1140
CGCCCTCAGC ATCTGGTGGA GCGAGGGCGA CAACATGAAC TGGCTCGACT CGGGCGAGGC  1200
CGGCCCCTGC GACCCGGACG AGGGCAACCC GTCCAACATC ATCCGCGTCC AGCCCGACCC  1260
GGAGGTCGTC TTCAGCAACC TGCGCTGGGG CGAGATCGGC TCAACCTACG AGTCCGCCGT  1320
CGACGGGCCC GTCGGCAAGG GCAAGGGCAA GGGCAAGGGC AAGGCTCCCG CCGGCGACGG  1380
CAACGGGAAG GAGAAGAGCA ATGGCAAGCG CTTCAGGAGG TTCTGAGCAA CCTTGATATT  1440
ATTTTTTTCT TTCTTTCCTT CACCAGTTAA TTAGTTGCCT TTGATTAGAA AGAGAGAGAG  1500
AAAACAAAGG GGAGTAGTAA TTAGACCACG ATGCTGCATA TAGAAAAAAA AAAAAAAAAA  1560
```

(2) INFORMATION FOR SEQ ID NO:3:

(i) SEQUENCE CHARACTERISTICS:
        (A) LENGTH: 402 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Gln Lys Pro Gly Glu Thr Lys Glu Val His Pro Gln Leu Thr Thr Phe
  1               5                  10                  15

Arg Cys Thr Lys Arg Gly Gly Cys Lys Pro Ala Thr Asn Phe Ile Val
             20                  25                  30

Asp Leu Ser Leu Ser His Pro Ile His Arg Ala Glu Gly Leu Gly Pro
         35                  40                  45

Gly Gly Cys Gly Asp Trp Gly Asn Pro Pro Lys Asp Val Cys Pro
     50                  55                  60
```

```
Asp Val Glu Ser Cys Ala Lys Asn Cys Ile Met Glu Gly Ile Pro Asp
 65                  70                  75                  80

Tyr Ser Gln Tyr Gly Val Thr Thr Asn Gly Thr Ser Leu Arg Leu Gln
             85                  90                  95

His Ile Leu Pro Asp Gly Arg Val Pro Ser Pro Arg Val Tyr Leu Leu
            100                 105                 110

Asp Lys Thr Lys Arg Arg Tyr Glu Met Leu His Leu Thr Gly Phe Glu
        115                 120                 125

Phe Thr Phe Asp Val Asp Ala Thr Lys Leu Pro Cys Gly Met Asn Ser
    130                 135                 140

Ala Leu Tyr Leu Ser Glu Met His Pro Thr Gly Ala Lys Ser Lys Tyr
145                 150                 155                 160

Asn Pro Gly Gly Ala Tyr Tyr Gly Thr Gly Tyr Cys Asp Ala Gln Cys
                165                 170                 175

Phe Val Thr Pro Phe Ile Asn Gly Leu Gly Asn Ile Glu Gly Lys Gly
            180                 185                 190

Ser Cys Cys Asn Glu Met Asp Ile Trp Glu Ala Asn Ser Arg Ala Ser
        195                 200                 205

His Val Ala Pro His Thr Cys Asn Lys Lys Gly Leu Tyr Leu Cys Glu
    210                 215                 220

Gly Glu Glu Cys Ala Phe Glu Gly Val Cys Asp Lys Asn Gly Cys Gly
225                 230                 235                 240

Trp Asn Asn Tyr Arg Val Asn Val Thr Asp Tyr Tyr Gly Arg Gly Glu
                245                 250                 255

Glu Phe Lys Val Asn Thr Leu Lys Pro Phe Thr Val Val Thr Gln Phe
            260                 265                 270

Leu Ala Asn Arg Arg Gly Lys Leu Glu Lys Ile His Arg Phe Tyr Val
        275                 280                 285

Gln Asp Gly Lys Val Ile Glu Ser Phe Tyr Thr Asn Lys Glu Gly Val
    290                 295                 300

Pro Tyr Thr Asn Met Ile Asp Asp Glu Phe Cys Glu Ala Thr Gly Ser
305                 310                 315                 320

Arg Lys Tyr Met Glu Leu Gly Ala Thr Gln Gly Met Gly Glu Ala Leu
                325                 330                 335

Thr Arg Gly Met Val Leu Ala Met Ser Ile Trp Trp Asp Gln Gly Gly
            340                 345                 350

Asn Met Glu Trp Leu Asp His Gly Glu Ala Gly Pro Cys Ala Lys Gly
        355                 360                 365

Glu Gly Ala Pro Ser Asn Ile Val Gln Val Glu Pro Phe Pro Glu Val
    370                 375                 380

Thr Tyr Thr Asn Leu Arg Trp Gly Glu Ile Gly Ser Thr Tyr Gln Glu
385                 390                 395                 400

Leu Gln
```

(2) INFORMATION FOR SEQ ID NO:4:

(i) SEQUENCE CHARACTERISTICS:
        (A) LENGTH: 196 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Ser Lys Pro Gly Leu Tyr Gly Cys Thr Gly Asp Glu Cys Gly Ser Ser
  1               5                  10                  15
```

```
        Gly Ile Cys Asp Lys Ala Gly Cys Gly Trp Asn His Asn Arg Ile Asn
                        20                  25                  30

Val Thr Asp Phe Tyr Gly Arg Gly Lys Gln Tyr Lys Val Asp Ser Thr
                    35                  40                  45

Arg Lys Phe Thr Val Thr Ser Gln Phe Val Ala Asn Lys Gln Gly Asp
                50                  55                  60

Leu Ile Glu Leu His Arg His Tyr Ile Gln Asp Asn Lys Val Ile Glu
         65                  70                  75                  80

Ser Ala Val Val Asn Ile Ser Gly Pro Pro Lys Ile Asn Phe Ile Asn
                        85                  90                  95

Asp Lys Tyr Cys Ala Ala Thr Gly Ala Asn Glu Tyr Met Arg Leu Gly
                        100                 105                 110

Gly Thr Lys Gln Met Gly Asp Ala Met Ser Arg Gly Met Val Leu Ala
                    115                 120                 125

Met Ser Val Trp Trp Ser Glu Gly Asp Phe Met Ala Trp Leu Asp Gln
                130                 135                 140

Gly Val Ala Gly Pro Cys Asp Ala Thr Glu Gly Asp Pro Lys Asn Ile
        145                 150                 155                 160

Val Lys Val Gln Pro Asn Pro Glu Val Thr Phe Ser Asn Ile Arg Ile
                        165                 170                 175

Gly Glu Ile Gly Ser Thr Ser Ser Val Lys Ala Pro Ala Tyr Pro Gly
                        180                 185                 190

Pro His Arg Leu
                    195

(2) INFORMATION FOR SEQ ID NO:5:

(i) SEQUENCE CHARACTERISTICS:
        (A) LENGTH: 200 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Asn Lys Lys Gly Leu Tyr Leu Cys Glu Gly Glu Cys Ala Phe Glu
        1               5                   10                  15

Gly Val Cys Asp Lys Asn Gly Cys Gly Trp Asn Asn Tyr Arg Val Asn
                        20                  25                  30

Val Thr Asp Tyr Tyr Gly Arg Gly Glu Glu Phe Lys Val Asn Thr Leu
                    35                  40                  45

Lys Pro Phe Thr Val Val Thr Gln Phe Leu Ala Asn Arg Arg Gly Lys
                50                  55                  60

Leu Glu Lys Ile His Arg Phe Tyr Val Gln Asp Gly Lys Val Ile Glu
         65                  70                  75                  80

Ser Phe Tyr Thr Asn Lys Glu Gly Val Pro Tyr Thr Asn Met Ile Asp
                        85                  90                  95

Asp Glu Phe Cys Glu Ala Thr Gly Ser Arg Lys Tyr Met Glu Leu Gly
                        100                 105                 110

Ala Thr Gln Gly Met Gly Glu Ala Leu Thr Arg Gly Met Val Leu Ala
                    115                 120                 125

Met Ser Ile Trp Trp Asp Gln Gly Asn Met Glu Trp Leu Asp His
                130                 135                 140

Gly Glu Ala Gly Pro Cys Ala Lys Gly Glu Gly Ala Pro Ser Asn Ile
        145                 150                 155                 160
```

```
              Val Gln Val Glu Pro Phe Pro Glu Val Thr Tyr Thr Asn Leu Arg Trp
                              165                 170                 175

Gly Glu Ile Gly Ser Thr Tyr Gln Glu Val Gln Lys Pro Lys Pro Lys
                          180                 185                 190

Pro Gly His Gly Pro Arg Ser Asp
                          195                 200

(2) INFORMATION FOR SEQ ID NO:6:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Thr Ala Thr Ala Cys Asp Ser Ala Gly Cys Gly Phe Asn Pro Tyr Gly
         1               5                   10                  15

Ser Gly Tyr Lys Ser Tyr Tyr Gly Pro Gly Asp Thr Val Asp Thr Ser
                         20                  25                  30

Lys Thr Phe Thr Ile Ile Thr Gln Phe Asn Thr Asp Asn Gly Ser Pro
                     35                  40                  45

Ser Gly Asn Leu Val Ser Ile Thr Arg Lys Tyr Gln Gln Asn Gly Val
         50                  55                  60

Asp Ile Pro Ser Ala Gln Pro Gly Gly Asp Thr Ile Ser Ser Cys Pro
         65                  70                  75                  80

Ser Ala Ser Ala Tyr Gly Gly Leu Ala Thr Met Gly Lys Ala Leu Ser
                         85                  90                  95

Ser Gly Met Val Leu Val Phe Ser Ile Trp Asn Asp Asn Ser Gln Tyr
                         100                 105                 110

Met Asn Trp Leu Asp Ser Gly Asn Ala Gly Pro Cys Ser Ser Thr Glu
                     115                 120                 125

Gly Asn Pro Ser Asn Ile Leu Ala Asn Asn Pro Asn Thr His Val Val
                     130                 135                 140

Phe Ser Asn Ile Arg Trp Gly Asp Ile Gly Ser Thr Thr Asn Ser Thr
         145                 150                 155                 160

Ala Pro Pro Pro Pro Ala Ser Ser Thr Thr Phe Ser Thr
                         165                 170

(2) INFORMATION FOR SEQ ID NO:7:

(i) SEQUENCE CHARACTERISTICS:
        (A) LENGTH: 204 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Thr Thr Val Gly Gln Glu Ile Cys Glu Gly Asp Gly Cys Gly Gly Thr
         1               5                   10                  15

Tyr Ser Asp Asn Arg Tyr Gly Gly Thr Cys Asp Pro Asp Gly Cys Asp
                         20                  25                  30

Trp Asn Pro Tyr Arg Leu Gly Asn Thr Ser Phe Tyr Gly Pro Gly Ser
                     35                  40                  45

Ser Phe Thr Leu Asp Thr Thr Lys Lys Leu Thr Val Val Thr Gln Phe
         50                  55                  60
```

-continued

```
Glu Thr Ser Gly Ala Ile Asn Arg Tyr Tyr Val Gln Asn Gly Val Thr
65                  70                  75                  80

Phe Gln Gln Pro Asn Ala Glu Leu Gly Ser Tyr Ser Gly Asn Glu Leu
                85                  90                  95

Asn Asp Asp Tyr Cys Thr Ala Glu Glu Ala Glu Phe Gly Gly Ser Ser
                100                 105                 110

Phe Ser Asp Lys Gly Gly Leu Thr Gln Phe Lys Lys Ala Thr Ser Gly
            115                 120                 125

Gly Met Val Leu Val Met Ser Leu Trp Asp Asp Tyr Tyr Ala Asn Met
        130                 135                 140

Leu Trp Leu Asp Ser Thr Tyr Pro Thr Asn Glu Thr Ser Ser Thr Pro
145                 150                 155                 160

Gly Ala Val Arg Gly Ser Cys Ser Thr Ser Ser Gly Val Pro Ala Gln
                165                 170                 175

Val Glu Ser Gln Ser Pro Asn Ala Lys Val Thr Phe Ser Asn Ile Lys
            180                 185                 190

Phe Gly Pro Ile Gly Ser Thr Gly Asn Pro Ser Gly
        195                 200
```

ALKALINE CELLULASES

CROSS-REFERENCE TO RELATED APPLICATION

This application is a continuation-in-part application of co-pending international application Ser. No. PCT/DK95/00108 filed Mar. 8, 1995, which is incorporated herein by reference.

BACKGROUND OF THE INVENTION

1. Field of the Invention

The present invention relates to a cellulase capable of removing soil from fabric, a cloned DNA sequence encoding for the cellulase, a detergent composition comprising the cellulase, a method of treating soiled fabric with the cellulolytic enzyme, and use of the cellulase e.g. in detergent compositions, in fabric softeners, for color clarification of textile fabrics (removal of fluffs and pills), for preventing backstaining in washing of fabric, for soil removal, for deinking of used paper, and for pulp recycling.

2. Description of the Related Art

Repeated washing of fabrics, especially cellulose containing fabrics, generally causes a harshness in the fabric used. The use of cellulases, i.e. cellulolytic enzymes, for harshness reduction of cellulose containing fabrics, e.g. cotton, was suggested and demonstrated a long time ago.

The practical exploitation of cellulases has, to some extent, been set back by the nature of the known cellulase preparations which are often complex mixtures of a variety of single cellulase components, and which may have a rather low specific activity. It is difficult to optimise the production of single components in multiple enzyme systems and thus to implement industrial cost-effective production of cellulases, and their actual use has been hampered by difficulties arising from the need to employ rather large quantities of the enzymes to achieve the desired effect.

The drawbacks of previously suggested cellulases may be remedied by using single-component enzymes selected for a high specific activity. Single-component cellulases are described in, e.g. WO 91/17243, WO 91/17244 and WO 91/10732.

For example, WO 91/17244 disclose a cellulose-degrading enzyme (a cellulase) derivable from a fungus other than Trichoderma or Phanerochaete which comprises a carbohydrate binding domain homologous to a terminal A region of *Trichoderma reesei* cellulases, the carbohydrate binding domain being capable of effecting binding of the enzyme to an insoluble cellulosic substrate, which may be employed for textile treatment, e.g. for reducing the harshness of cotton-containing fabrics and for soil removal and color clarification of fabrics. Example 3 and FIG. 13 disclose the preparation of a *Fusarium oxysporum* C-family endoglucanase and the DNA sequence and derived amino acid sequence thereof, respectively. Later it was found that the disclosed amino acid sequence was not correct; the corrected sequence is published in Sheppard, P. O., Grant, F. J., Oort, P. J., Sprecher, C. A., Foster, D. C., Hagen, F. S., Upshall, A., Mcknight, G. L. and Ohara, P. J.: The use of conserved cellulase family-specific sequences to clone cellulase homolog cdnas from *Fusarium oxysporum. Gene*, 150:163–167, 1994. Example 4 and FIGS. 14A–E disclose the preparation of a *Humicola insolens* endoglucanase 1 (EG I) and the DNA sequence and derived amino acid sequence thereof, respectively. Further, in example 4 (page 32, line 1 to 5) is described the construction of expression plasmid of a truncated EG I (denoted EG I') wherein the last 13 amino acids of the coding region were eliminated and the altering of Val to Leu in position 421 (position 401 in the sequence of the enzyme). The gist of the invention disclosed in WO 91/17244 is to provide a cellulase which, besides the enzyme core, has a carbohydrate binding domain (CBD) which is homologous to the A region of *Trichoderma reesei* cellulases, since the function of the CBD in the enzyme molecule was believed to be to mediate binding to solid substrates including cellulose and consequently to enhance the activity of such enzymes towards such substrates.

The problem underlying the present invention is to obtain single-component endoglucanases having enhanced enzyme activity in the alkaline pH range, while at the same time exerting a moderate cellulolytic action on the cellulosic substrate. In other words, the endoglucanase should neither destroy the cellulosic substrate as such. For example, when the substrate is a cellulosic fabric, the used endoglucanase should not result in a substantial tensile strength loss of the fabric. The enhanced alkaline activity of the enzyme is also essential, since most applications of endoglucanases advantageously take place in the alkaline pH range.

SUMMARY OF THE INVENTION

Surprisingly, it has now been found that certain cellulases which do not comprise a carbohydrate binding domain, i.e. essentially consist of the core enzyme, or which at least do not comprise a carbohydrate binding domain which is homologous to the A region of *Trichoderma reesei* cellulases, may have an enhanced activity. This may for example result in improved soil removal from fabrics.

Preferably, the cellulases of the invention are endoglucanases which have the amino acid residue tryptophan (Trp or W) in the position corresponding to position 55 of the structural homology frame in FIG. 1.

More specifically, it has been found that certain cellulases, preferably endoglucanases, which can be derived from the strain *Myceliophthora thermophila*, especially to *Myceliophthora thermophila*, CBS 117.65, and which comprise a core and optionally a C-terminal link consisting of 10 amino acids at the most may perform excellent in detergents with respect to soil removal in comparison with the known cellulases.

The present endoglucanases are useful e.g. for soil removal and may thus be applied to detergent compositions, detergent additives and/or fabric softeners.

Other uses of the present endoglucanases are for color clarification of textile fabrics (removal of fluffs and pills), for preventing backstaining in washing of fabric, for soil removal, for deinking of used paper, and for pulp recycling.

In a further aspect, the invention relates to a cloned DNA sequence encoding for an enzyme having cellulolytic activity, especially an endoglucanase, which DNA sequence comprises the DNA sequence shown in SEQ ID NO:2 or an analogue of the DNA sequence shown in SEQ ID NO:2 which i) is homologous, preferably at least 60% homologous, with the DNA sequence shown in SEQ ID NO:2;

ii) hybridizes under the conditions described herein with the same nucleotide probe as the DNA sequence shown in SEQ ID NO:2;

iii) encodes a polypeptide which is homologous, preferably at least 60% homologous, with the polypeptide encoded by a DNA sequence comprising the DNA sequence shown in SEQ ID NO:2; or iv) encodes a polypeptide which is immunologically reactive with an antibody raised against the purified endoglucanase encoded by the DNA sequence shown in SEQ ID NO:2.

Figure 1A:
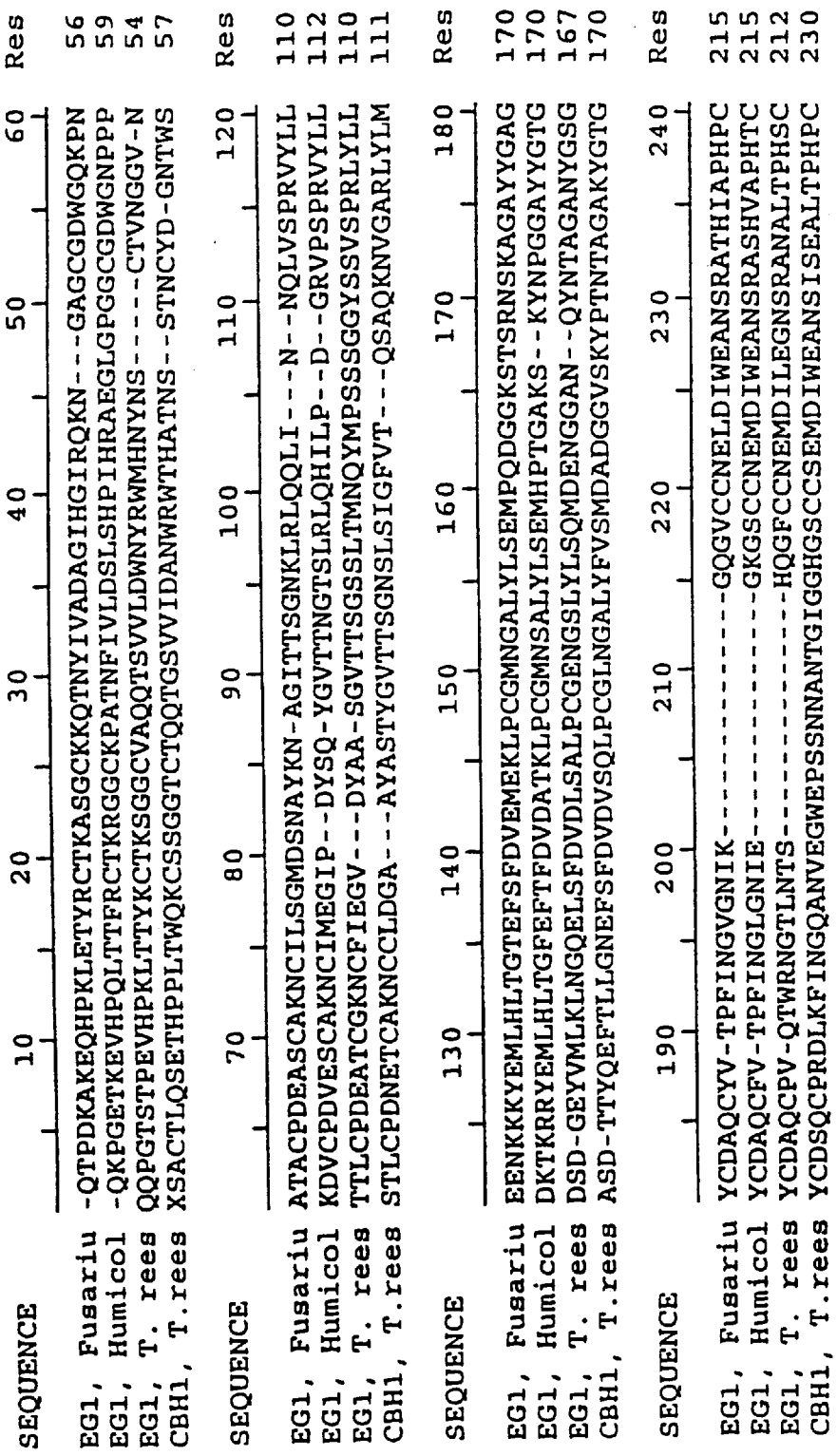
FIG. 1 shows the alignment of the amino acid sequences of three endoglucanases and one cellobiohydrolase.

EG1-F: *Fusarium oxysporum* endoglucanase EG1 (fus_eg1_nat.pdb, a-chain) (SEQ ID NO:4)

EG1-H: *Humicola insolens* endoglucanase EG1 (1egi.pdb, a-chain) (SEQ ID NO:5)

EG1-T: *Trichoderma reesei* endoglucanase EG1 (no pdb structure) (SEQ ID NO:6)

CBH1: *Trichoderma reesei* cellobiohydrolase (1cel.pdb, a-chain) (SEQ ID NO:7)

DETAILED DESCRIPTION OF THE INVENTION

In the present specification and claims, the term "cellulase" denotes an enzyme that hydrolyses cellulose. The cellulase may be a component occurring in a cellulase system produced by a given microorganism, such a cellulase system mostly comprising several different cellulase enzyme components including those usually identified as e.g. cellobiohydrolases, exo-cellobiohydrolases, endoglucanases, β-glucosidases. Alternatively, the cellulase may be a single component, i.e. a component essentially free of other cellulase components usually occurring in a cellulase system produced by a given microorganism, the single component being a recombinant component, i.e. produced by cloning of a DNA sequence encoding the single component and subsequent cell transformed with the DNA sequence and expressed in a host. The host is preferably a heterologous host, but the host may under certain conditions also be the homologous host.

In a preferred embodiment of the invention, the cellulase is an endoglucanase.

The term "soil removal" or "particulate soil removal", as used herein, refers to enhanced cleaning of cellulose-containing fabrics or garment, e.g. cotton, contaminated by particles of soil or of other insoluble matter entrapped by microfibrills spreading out on the fiber surface.

In the present context, the term "homologous" or "homologous sequence" is intended to indicate an amino acid sequence differing from those of SEQ ID NO:1, SEQ ID NO:3, or FIG. 1, respectively, by one or more amino acid residues. The homologous sequence may be one resulting from modification of an amino acid sequence shown in these sequences, e.g. involving substitution of one or more amino acid residues at one or more different sites in the amino acid sequence, deletion of one or more amino acid residues at either or both ends of the enzyme or at one or more sites in the amino acid sequence, or insertion of one or more amino acid residues at one or more sites in the amino acid sequence. The modification of the amino acid sequence may suitably be performed by modifying the DNA sequence encoding the enzyme, e.g. by site-directed or by random mutagenesis or a combination of these techniques in accordance with well-known procedures. Alternatively, the homologous sequence may be one of an enzyme derived from another origin than the cellulases corresponding to the amino acid sequences shown in of SEQ ID NO:1, SEQ ID NO:3, or FIG. 1, respectively. Thus, "homologue" may e.g. indicate a polypeptide encoded by DNA which hybridizes to the same probe as the DNA coding for the cellulase with the amino acid sequence in question under certain specified conditions (such as presoaking in 5×SSC and prehybridising for 1 h at ~40° C. in a solution of 20% formamide, 5×Denhardt's solution, 50 mM sodium phosphate, pH 6.8, and 50 µg of denatured sonicated calf thymus DNA, followed by hybridization in the same solution supplemented with 100 µM ATP for 18 h at ~40° C.). The homologous sequence will normally exhibit a degree of homology (in terms of identity) of at least 50%, such as at least 60%, 65%, 70%, 75%, 80%, 85%, 90% or even 95% with the amino acid sequences shown in of SEQ ID NO:1, SEQ ID NO:3, or FIG. 1, respectively.

Preferably, the degree of homology is based on three-dimensional structural homology of the cellulases. For example, FIG. 1 shows the alignment of the amino acid sequences of three endoglucanases and one cellobiohydrolase:

EG1-F: *Fusarium oxysporum* endoglucanase EG1 (fus_eg1_nat.pdb, a-chain) (SEQ ID NO:4)

EG1-H: *Humicola insolens* endoglucanase EG1 (1egi.pdb, a-chain) (SEQ ID NO:5)

EG1-T: *Trichoderma reesei* endoglucanase EG1 (no pdb structure) (SEQ ID NO:6)

CBH1: *Trichoderma reesei* cellobiohydrolase (1cel.pdb, a-chain) (SEQ ID NO:7)

The references in the brackets refer to the Brookhaven Database identification for entries.

Initially the sequences were aligned based on secondary structure homology, but superimposition and visual examination of the X-ray structures of EG1-F, EG1-H and CBH1 necessitated several modifications of the sequence alignment. The final output in FIG. 1 is based on three-dimensional structural alignment.

The C-terminals are visible to different extents in the three crystal structures. Following the common sequence motif IGST (Res#445–449), three residues are visible in EG1-F, one in EG1-H, and five in CBH1. For the sequence comparison in Table 1 below, residues from the N-terminals to the C-terminal motif NPSG in CBH1 are included (Res#453 in FIG. 1), i.e. 402 residues from EG1-F and EG1-H, 373 residues from EG1-T and 434 residues from CBH1.

TABLE 1

Sequence identities calculated relative to the lengths of each one of the sequences (seq1 & seq2)

| seq1\seq2 | EG1-H | EG1-T | CBH1 |
| --- | --- | --- | --- |
| EG1-F | 58% & 58% | 41% & 44% | 41% & 38% |
| EG1-H | ********* | 41% & 44% | 40% & 37% |
| EG1-T | ********* | ********* | 47% & 40% |

In Table 2 below is listed the disulfide bridges found in EG1-F, EG1-H and CBH1. Based on structural homology the equivalent positions for EG1-T are indicated.

TABLE 2

Disulfide bridges in EG1-F, EG1-H and CBH1. Based on the sequence alignment in FIG. 1, the equivalent positions are indicated for EG1-T. The numbers refer to those in FIG. 1

| Res# (FIG. 1) | EG1-F | EG1-H | (EG1-T) | CBH1 |
| --- | --- | --- | --- | --- |
| 4–75 | * | * | * | 4–72 |
| 19–25 | 18–24 | 18–24 | 19–25 | 19–25 |

TABLE 2-continued

Disulfide bridges in EG1-F, EG1-H and CBH1. Based on the sequence alignment in FIG. 1, the equivalent positions are indicated for EG1-T. The numbers refer to those in FIG. 1

| Res# (FIG. 1) | EG1-F | EG1-H | (EG1-T) | CBH1 |
|---|---|---|---|---|
| 52–74 | 48–70 | 51–73 | 47–68 | 50–71 |
| 64–70 | 60–66 | 63–69 | 58–64 | 61–67 |
| 148–416 | 138–365 | 140–365 | 137–336 | 138–397 |
| 182–220 | 172–195 | 172–195 | 169–192 | 172–210 |
| 186–219 | 176–194 | 176–194 | 173–191 | 176–209 |
| 240–266 | 215–234 | 215–234 | 212–? | 230–256 |
| 248–253 | 223–228 | 223–228 | 217–222 | 238–243 |
| 271–350 | 239–315 | 239–315 | ?–291 | 261–331 |

EG1-H and EG1-F contain the same 9 disulfide bridges.

The deletion around Res#260 in EG1-T prevents the formation of two disulfide bridges: C215–C234 & C239–C315 (EG1-H numbering). It is possible that the EG1-T structure has moved relative to EG1-H and EG1-F to enable the formation of a disulfide bridge between C215 and C315 (C212 & C291 in EG1-T numbering). The remaining 7 disulfide bridges found in EG1-F and EG1-H are also present in EG1-T.

CBH1 contains the same 9 disulfide bridges as EG1-F and EG1-H, and one additional disulfide bridge in the N-terminal region.

CBH1 contains the most insertions relative to the others, and these insertions are predominantly located at the edges of the substrate binding cleft, possibly contributing to the fact that CBH1 is a cellobiohydrolase.

When attempting to explain the improved alkaline activity of EG1-H and EG1-F relative to EG1-T, the following loops may be the most interesting, as they contain charges in the proximity of the active site. Charges can alter the pKa values of the catalytic residues, and interact with the transfer of electrons during catalysis.

a) the 11-residue insertions (relative to EG1-T) at pos. 229 in EG1-H and EG1-F (Res#254) are located above the active site residues (E197, D199 & E202) and contain 2 or 3 charged residues.
   b) the 5-residue insertions (relative to EG1-T) at pos. 320 in EG1-H and EG1-F (Res#355) are located at the end of the substrate binding pocket and contain 2 or 3 charged residues.
   c) the 2-residue insertions (relative to EG1-T) at pos. 259 in EG1-H and EG1-F (Res#291) are located close to the b) insertion above, and contain a charged lysine residue.

The amino acid compositions of the four enzymes, i.e. EG1-F, EG1-H, EG1-T and CBH1) including the residues used in the sequence identity Table 1 above (i.e. including Res#453), are shown in Table 3.

TABLE 3

Amino acid compositions & pKa values used for pI calculation

| | EG1-F | EG1-H | EG1-T | CBH1 | pKa |
|---|---|---|---|---|---|
| Asp | 21 | 18 | 19 | 24 | 3.5 |
| Asn | 28 | 22 | 34 | 30 | — |
| Thr | 22 | 28 | 34 | 46 | — |
| Ser | 26 | 17 | 46 | 50 | — |
| Glu | 20 | 31 | 10 | 19 | 4.0 |
| Gln | 18 | 12 | 16 | 18 | — |
| Pro | 17 | 24 | 18 | 19 | — |
| Gly | 44 | 47 | 43 | 51 | — |
| Ala | 31 | 20 | 22 | 27 | — |
| Val | 21 | 24 | 19 | 21 | — |
| Cys | 18 | 18 | 16 | 20 | 9.3 |
| Met | 11 | 11 | 9 | 6 | — |
| Ile | 22 | 14 | 11 | 10 | — |
| Leu | 20 | 25 | 23 | 24 | — |
| Tyr | 16 | 19 | 19 | 20 | 9.9, 11.6 or 12.5 |
| Phe | 9 | 15 | 8 | 15 | — |
| Lys | 31 | 23 | 9 | 13 | 10.0 |
| His | 8 | 10 | 5 | 4 | 6.4 |
| Trp | 6 | 7 | 6 | 9 | — |
| Arg | 13 | 17 | 6 | 7 | 12.8 |

Assumed pKa's for Tyr 50% pH 9.9, 25% pH 11.6 & 25% Ph 12.5.

The isoelectric points (pI) were estimated for each of the four cellulases (shown in Table 4 below), employing standard pKa values. It was assumed that the N-terminals are blocked, that no free C-terminal is present in the core enzymes, and that no metal ions are bound. The calculations do not consider the effects of deaminations.

TABLE 4

Isoelectric point

| | pI calculated | pI found |
|---|---|---|
| EG1-F | 8.9 | about 9 |
| EG1-H | 5.7 | about 5 |
| EG1-T | 4.0 | |
| CBH1 | 3.8 | |

The difference between the calculated and actual pI values may be due to deaminating, e.g. Asn to Asp, which lower the actual pI.

From the amino acid compositions and the pKa values it is possible to calculate at different pH values the (partial) charges on all titrable amino acids. In this way the net charges and the sum of positive and negative charges were calculated at pH 4, 6, 8 and 10, as shown in Table 5.

The two alkaline cellulases, EG1-H and EG1-F, share the common characteristic, that over a broad pH-interval (pH 4–10) they contain at least 70 charged residues. The acidic EG1-T in contrast contains fewer than 50 charged residues within this pH-interval. The more densely charged surfaces of EG1-F and EG1-H may be responsible for the improved performance in laundry detergents relative to EG1-T.

TABLE 5

Charges as a function of pH. The first number is the net charge (e.g. (+13) + (−17) = −4), the second is the total number of charges (e.g. |+13| + |−17| = +30)

| | EG1-F | EG1-H | EG1-T | CBH1 |
|---|---|---|---|---|
| pH 4 | +26/78 | +21/79 | +1/39 | −4/52 |
| pH 6 | +9/90 | −1/96 | −10/47 | −20/66 |
| pH 8 | +3/85 | −9/89 | −14/44 | −23/63 |
| pH 10 | −17/74 | −26/83 | −24/45 | −35/62 |

To examine the active site region in more detail, amino acids located within 10 Å of the active site residues E197, D199 and E202 were identified for EG1-H and EG1-F. The following residues belong to this 10 Å subset in EG1-H (EG1-H numbering): 108, 124, 129, 131, 133, 135, 138–139, 141–151, 171–177, 193–220, 233–243, 245, 252, 266, 268, 270, 272, 280, 283, 285, 287, 310, 323, 326, 328, 331–336, 338–347, 354, 356–358, 362, 384 and 386.

The 10 Å subset in EG1-F contain essentially the same residues as EG1-H 10 Å subset. EG1-T differs more significantly, in particular with respect to the segments around 219–221 and 230–240 in EG1-H and EG1-F, which are absent in EG1-T. Approx. 80% sequence identity exists between EG1-F and EG1-H within the 10 Å subset, whereas the residues in the equivalent 10 Å subset for EG1-t are more different. Of particular interest are differences involving charges.

Within the 10 Å subset a number of mutations in EG1-H & EG1-F, aiming at affecting catalysis by changing electrostatics, are contemplated based on sequence homology to EG1-T. To decrease pI within this region M142E, K217A, K218T (in EG1-H only) and R245G is contemplated, and to increase pI E150Q, I310D, E334K (in EG1-H) and D334K (in EG1-F) are contemplated.

The following amino acid residues are in close contact with cellobiose (bound to the EG1-F); the numbering refers to the EG1-F numbering:

Hydrogen bonding between enzyme and inhibitor a) R106 conserved in all 4 cellulases b) Y145 conserved in all 4 cellulases c) S345 conserved in all 4 cellulases Within 5 Å of cellubiose (excluding three active site residues, and the three H-bonding residues above)

d) D34 conserved in all 4 cellulases e) W51 also W51 in EG1-H. This W appears to be important for binding of the second sugar moiety in cellubiose (relative to the active site).

f) S104 conserved in all EG1s g) A143 also A143 in EG1-H h) Y171 conserved in all 4 cellulases i) D173 conserved in all 4 cellulases j) Q175 conserved in all 4 cellulases k) Y177 not conserved l) W347 conserved in all 4 cellulases. This W347 appears to be important for binding of the first sugar moiety in cellobiose (relative to the active site).

Most of these residues are highly conserved. This implies that mutating them may be not of any advantage, but it certainly does not mean that the performance of EG1s cannot be improved by replacement of these residues. They are all located in the active site region, and in fact this makes them very interesting, as property changes are likely to be more significant. Therefore, it is contemplated that substitutions at all these positions are preferred substitutions.

The advantage of EG1-H is its ability to induce soil removal with minimal fabric damage. What is characteristic about EG1-H and EG1-F compared to Carezyme (4egv.pdb) and *Thermomonospora fusca* EG1 is a comparatively deep substrate binding cleft, possibly preventing the access of intact cotton fibers into the catalytic site.

In EG1-F and EG1-H the substrate binding cleft is 18–20 Å deep when measuring the distances between the Cα atoms of the active site residues (E197, D199 & E202) and the Cα atoms of the residues located at the upper rim of the substrate binding pocket (G351 & A229 in EG1-H). The pocket is approx 19 Å wide, when measuring between Cα atoms of the two rim residues.

In contrast, the depth of the substrate binding pocket in Carezyme® (4egv.pdb), when measured in a similar manner, is only 8–10 Å, whereas the width at the rim is approx. 9 Å.

In *T. fusca* EG1 (1tml.pdb) the depth of the pocket is approx. 10 Å, and the width approx. 18 Å.

The present invention relates to a cellulase which is selected from the group consisting of cellulases classified in family 7 as described in Henrissat, B. et al.: *Biochem. J.* (1993), 293, p. 781–788, and cellulase variants derived from a parent cellulase classified in family 7.

The classification by Henrissat is a new classification system for glycosyl hydrolases based on sequence comparisons and hydrophobic cluster analyses which have shown that the catalytic domains of glycosyl hydrolases fall into 45 distinct families, of which 11 (originally denoted A–K) contain enzymes with cellulolytic activity.

Thus far, structures of the catalytic domains of cellulases from four families have been published:

Cellobiohydrolase II (CBH II) from *Trichoderma reesei* (Rouvinen et al. 1990) and endocellulase E2 from *Thermomonospora fusca* (Sapezio et al. 1993) from family 6(B), Cellobiohydrolase I (CBH I) from *T. reesei* (Divine et al. 1994) from family 7 (C), CelA from *Clostridium thermocellum* (Juy et al. 1992) from family 9(E); and the endglcucanase V from *H. insolens* (Davies et al. 1993) from family 45(K).

The cellulases of the invention may be obtainable by or derived from a strain of Myceliophthora, preferably from a strain of *Myceliophthora thermophila*.

In the present context, the "analogue" of the DNA sequence shown in SEQ ID No. 2 is intended to indicate any DNA sequence encoding an enzyme exhibiting endoglucanase activity, which has any or all of the properties i)–iv). The analogous DNA sequence a) may be isolated from another or related (e.g. the same) organism producing the enzyme with endoglucanase activity on the basis of the DNA sequence shown in SEQ ID No 2, e.g. using the procedures described herein; the homologue may be an allelic variant of the DNA sequence comprising the DNA sequences shown herein, i.e. an alternative form of a gene that arises through mutation; mutations can be silent (no change in the encoded enzyme) or may encode enzymes having altered amino acid sequence; the homologue of the present DNA sequence may also be a genus or species homologue, i.e. encoding an enzyme with a similar activity derived from another species, b) may be constructed on the basis of the DNA sequences shown in SEQ ID No. 2, e.g. by introduction of nucleotide substitutions which do not give rise to another amino acid sequence of the endoglucanase encoded by the DNA sequence, but which correspond to the codon usage of the host organism intended for production of the enzyme, or by introduction of nucleotide substitutions which may give rise to a different amino acid sequence. However, in the latter case amino acid changes are preferably of a minor nature, that is conservative amino acid substitutions that do not significantly affect the folding or activity of the protein, small deletions, typically of one to about 30 amino acids; small amino- or carboxyl-terminal extensions, such as an amino-terminal methionine residue, a small linker peptide of up to about 20–25 residues, or a small extension that facilitates purification, such as a poly-histidine tract, an antigenic epitope or a binding domain. See in general Ford et al., *Protein Expression and Purification* 2: 95–107, 1991. Examples of conservative substitutions are within the group of basic amino acids (such as arginine, lysine, histidine), acidic amino acids (such as glutamic acid and aspartic acid), polar amino acids (such as glutamine and asparagine), hydrophobic amino acids (such as leucine, isoleucine, valine), aromatic amino acids (such as phenylalanine, tryptophan, tyrosine) and small amino acids (such as glycine, alanine, serine, threonine, methionine).

It will be apparent to persons skilled in the art that such substitutions can be made outside the regions critical to the function of the molecule and still result in an active polypeptide. Amino acids essential to the activity of the polypeptide encoded by the DNA construct of the invention, and therefore preferably not subject to substitution, may be identified according to procedures known in the art, such as site-directed mutagenesis or alanine-scanning mutagenesis (Cunningham and Wells, *Science* 244, 1081–1085, 1989). In the latter technique mutations are introduced at every residue in the molecule, and the resultant mutant molecules are tested for biological (i.e. endoglucanase) activity to identify amino acid residues that are critical to the activity of the molecule. Sites of substrate-enzyme interaction can also be determined by analysis of crystal structure as determined by such techniques as nuclear magnetic resonance, crystallography or photoaffinity labeling. See, for example, de Vos et al., *Science* 255: 306–312, 1992; Smith et al., *J. Mol. Biol.* 224: 899–904, 1992; Wlodaver et al., *FEBS Lett.* 309: 59–64, 1992.

The endoglucanase encoded by the DNA sequence of the DNA construct of the invention may comprise a cellulose binding domain (CBD) existing as an integral part of the encoded enzyme, or a CBD from another origin may be introduced into the endoglucanase enzyme thus creating an enzyme hybride. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains (CBDs) into 10 families (I–X), and it demonstrates that CBDs are found in various enzymes such as cellulases, xylanases, mannanases, arabinofuranosidases, acetyl esterases and chitinases. CBDs have also been found in algae, e.g., the red alga *Porphyra purpurea* as a non-hydrolytic polysaccharide-binding protein, for reference see Peter Tomme et al., supra. However, most of the CBDs are from cellulases and xylanases. CBDs are found at the N or C termini of proteins or are internal. Enzyme hybrids are known in the art, see e.g. WO 90/00609 and WO 95/16782, and may be prepared by transforming into a host cell a DNA construct comprising at least a fragment of DNA encoding the cellulose-binding domain ligated, with or without a linker, to a DNA sequence encoding the enzyme of interest and growing the host cell to express the fused gene. Enzyme hybrids may be described by the following formula:

CBD-MR-X, wherein CBD is the N-terminal or the C-terminal region of an amino acid sequence corresponding to at least the cellulose-binding domain; MR is the middle region (the linker), and may be a bond, or a short linking group preferably of from about 2 to about 100 carbon atoms, more preferably of from 2 to 40 carbon atoms; or is preferably from about 2 to about 100 amino acids, more preferably of from 2 to 40 amino acids; and X is an N-terminal or C-terminal region of a polypeptide encoded by the DNA sequence of the invention.

The homology referred to in i) above is determined as the degree of identity between the two sequences indicating a derivation of the first sequence from the second. The homology may suitably be determined by means of computer programs known in the art such as GAP provided in the GCG program package (Needleman, S. B. and Wunsch, C. D., *Journal of Molecular Biology*, 48: 443–453, 1970). Using GAP with the following settings for DNA sequence comparison: GAP creation penalty of 5.0 and GAP extension penalty of 0.3, the coding region of the DNA sequence exhibits a degree of identity preferably of at least 60%, more preferably at least 65%, more preferably at least 70%, even more preferably at least 80%, especially at least 90%, with the coding region of the DNA sequence shown in SEQ ID No. 2.

The hybridization referred to in ii) above is intended to indicate that the analogous DNA sequence hybridizes to the same probe as the DNA sequence encoding the endoglucanase enzyme under certain specified conditions which are described in detail in the Materials and Methods section hereinafter. The oligonucleotide probe to be used is the DNA sequence corresponding to the endoglucanase encoding part of the DNA sequence shown in SEQ ID NO 2.

The homology referred to in iii) above is determined as the degree of identity between the two sequences indicating a derivation of the first sequence from the second. The homology may suitably be determined by means of computer programs known in the art such as GAP provided in the GCG program package (Needleman, S. B. and Wunsch, C. D., *Journal of Molecular Biology*, 48: 443–453, 1970). Using GAP with the following settings for polypeptide sequence comparison: GAP creation penalty of 3.0 and GAP extension penalty of 0.1, the polypeptide encoded by an analogous DNA sequence exhibits a degree of identity preferably of at least 60%, more preferably at least 65%, even more preferably at least 70%, more preferably at least 80%, especially at least 90%, with the enzyme encoded by a DNA construct comprising the DNA sequence shown in SEQ ID No. 2.

In connection with property iv) above it is intended to indicate an endoglucanase encoded by a DNA sequence isolated from strain *Myceliophthora thermophila*, preferably *Myceliophthora thermophila*, CBS 117.65, and produced in a host organism transformed with said DNA sequence or the corresponding endoglucanase naturally produced by *Myceliophthora thermophila*. The immunological reactivity may be determined by the method described below.

In further aspects the invention relates to an expression vector harbouring a cloned DNA sequence of the invention, a cell comprising the cloned DNA sequence or expression vector and a method of producing an enzyme exhibiting endoglucanase activity which method comprises culturing said cell under conditions permitting the production of the enzyme, and recovering the enzyme from the culture.

In a still further aspect the invention relates to an enzyme exhibiting endoglucanase activity, which enzyme a) is encoded by a cloned DNA sequence of the invention b) produced by the method of the invention, and/or c) is immunologically reactive with an antibody raised against a purified endoglucanase encoded by the DNA sequence shown in SEQ ID No. 2.

The endoglucanase mentioned in c) above may be encoded by the DNA sequence isolated from the strain *Myceliophthora thermophila* and produced in a host organism transformed with said DNA sequence or the corresponding endoglucanase naturally produced by *Myceliophthora thermophila*.

The cellulase of the invention can advantageously have one or more insertions of between 1 and 25, preferably between 1 and 20, amino acid residues; preferably the insertion is relative to EG1-Tat position 230–240 in EG1-H and EG1-F and part of which is located within 10 Å of the active site residues E197, D199 and E202.

In another aspect, the cellulase of the invention has a substrate binding cleft with a depth of at least 12 Å, preferably 15 Å, when measuring between Cα atoms of the active site residues located at the bottom of the cleft and Cα atoms of residues located at the rim of the substrate binding cleft immediately above the active site residues.

According to the invention, cellulases which essentially consists of the core and optionally a C-terminal link having 10 amino acids at the most may perform excellent for particulate soil removal when used for washing/laundry or fabric softening purposes. SEQ ID NO:1 is the amino acid sequence of an endoglucanase from *Myceliophthora thermophila*. The protein sequence (of SEQ ID No:1) starts at position 21; the last 36 amino acids form a tail which will be removed by proteases. Without being bound to the theory it is believed that an enhanced enzyme activity may be obtained by providing cellulases, especially endoglucanases, which essentially consists of a core. The cellulase may further comprise a C-terminal link, a "tail", which is relatively short, the short C-terminal link not contributing negatively to the enzyme activity. Thus it is believed that cellulases of the invention may be derived from known cellulases e.g. by "truncating" the C-terminal wholly or partly from the enzyme protein in question.

It is contemplated that cellulases which have an amino acid sequence being at least 60% homologous with the amino acid sequences listed in SEQ ID Nos. 1 and 3, respectively, also have enhanced activity resulting in improved soil removal from fabrics.

The pI of the cellulase from *Myceliophthora thermophila* was found to be 4.0.

Examples of variants of these cellulases are variants wherein one or more of the following amino acid residue, if present, are substituted: N89Q, N89Q+N247Q, H123N, T385N, Q399N, E202A, S37W+P39W.

Other useful variants are those wherein one or more of the following amino acid residues, if present, are substituted: M142E, K217A, K217A+K218T, R245G, I310D, E150Q, E334K, M198L.

Yet other useful cellulase variant are those wherein one or more of the following amino acid residues, if present, within 5 Å of bound cellobiose are substituted: R106x, Y145x, S345x, D34x, W51x, S104x, A143x, Y171x, D173x, Q175x, Y177x, W347x, where x is chosen to modify H-bonding potential and/or hydrophobic interaction with the substrate.

The activity of the present cellulases with respect to soil removal may be correlated to specific analytical methods.

Accordingly, a useful cellulase may have high activity on cellotriose in the presence of a detergent matrix, high dispersing action on carbon black, and high alkaline activity on acid swollen cellulose at pH 8.

More specifically, the activity on cellotriose (see below) in the presence of a detergent matrix corresponds to an apparent $k_{cat}$ at pH 8 of preferably at least 1 per sec; the dispersing action on carbon black at pH 10 corresponds to a delta value preferably of at least 0.20 measured at 582 nm for 5 mg/l of cellulase (see e.g. example 2); and the alkaline activity on acid swollen cellulose at pH 8 corresponds to an apparent $k_{cat}$ preferably of at least 10 per sec (see below).

EG I* (from *Humicola insolens*) has an apparent molecular weight (MW) of about 50 kD due to glycosylation of the molecule. It is believed that the "true" MW is about 46 kD. The pI of EG I* is at least about 0.4 lower than of EG I, since pI of EG I* is about 5.1–5.3 whereas pI of EG I is about 5.5–6.2.

EGI-Fus (from *Fusarium oxysporum*) has a apparent molecular weight (MW) of 48 kD; the amino acid composition gives 45 kD with 2 N glycosylation sites. The actual pI is above 9, and the theoretical pI is 9 which has been calculated based on the amino acid composition and using the pKa values from C. Tanford in Adv. Protein Chem., Vol. 17, pages 69–165, 1962. The molar extinction coefficient (based on the amino acid composition) has been calculated to 58180.

It has been found that the stability of EGI-Fus is optimal at 50 degrees Celsius. The enzyme exhibits no activity above 60 degrees Celsius. The catalytic activity on cellotriose at pH 8.5 and 40° C. has been calculated to 5.5 $K_{cat}$ per sec. Km is 0.5 mM. Further, the activity on CMC is about 315 ECU per mg protein. The activity of EGI-Fus can be inactivated by 3-epoxybutyl cellobioside; see e.g. G. Legler and E. Bause, Carbohydrate Research vol 28 (1973) page 45–52: Epoxyalkyl oligo (1–4) beta-D-Glucosides as active site directed inhibitors of cellulases.

The cellulases of the invention may be obtained from the microorganism in question by use of any suitable technique. For instance, a cellulase preparation may be obtained by fermentation of a microorganism and subsequent isolation of a cellulase containing preparation from the fermented broth or microorganism by methods known in the art, but more preferably by use of recombinant DNA techniques as known in the art. Such method normally comprises cultivation of a host cell transformed with a recombinant DNA vector capable of expressing and carrying a DNA sequence encoding the cellulase component in question, in a culture medium under conditions permitting the expression of the enzyme and recovering the enzyme from the culture.

Cloning a DNA sequence encoding a cellulase

The DNA sequence encoding a parent cellulase may be isolated from any cell or microorganism producing the cellulase in question by various methods, well known in the art. First a genomic DNA and/or cDNA library should be constructed using chromosomal DNA or messenger RNA from the organism that produces the cellulase to be studied. Then, if the amino acid sequence of the cellulase is known, homologous, labelled oligonucleotide probes may be synthesized and used to identify cellulase-encoding clones from a genomic library of bacterial DNA, or from a fungal cDNA library. Alternatively, a labelled oligonucleotide probe containing sequences homologous to cellulase from another strain of bacteria or fungus could be used as a probe to identify cellulase-encoding clones, using hybridization and washing conditions of lower stringency.

Yet another method for identifying cellulase-producing clones would involve inserting fragments of genomic DNA into an expression vector, such as a plasmid, transforming cellulase-negative bacteria with the resulting genomic DNA library, and then plating the transformed bacteria onto agar containing a substrate for cellulase. Those bacteria containing cellulase-bearing plasmid will produce colonies surrounded by a halo of clear agar, due to digestion of the substrate by secreted cellulase.

Alternatively, the DNA sequence encoding the enzyme may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *The EMBO J.* 3, 1984, pp. 801–805. According to the phosphoamidite method, oligonucleotides are synthesized, e.g. in an automatic DNA synthesizer, purified, annealed, ligated and cloned in appropriate vectors.

Finally, the DNA sequence may be of mixed genomic and synthetic, mixed synthetic and cDNA or mixed genomic and cDNA origin prepared by ligating fragments of synthetic, genomic or cDNA origin (as appropriate), the fragments corresponding to various parts of the entire DNA sequence, in accordance with standard techniques. The DNA sequence may also be prepared by polymerase chain reaction (PCR) using specific primers, for instance as described in U.S. Pat. No. 4,683,202 or R. K. Saiki et al., Science 239, 1988, pp. 487–491.

Expression of cellulase variants

According to the invention, a mutated cellulase-coding sequence produced by methods described above, or any alternative methods known in the art, can be expressed, in enzyme form, using an expression vector which typically includes control sequences encoding a promoter, operator, ribosome binding site, translation initiation signal, and, optionally, a repressor gene or various activator genes. To permit the secretion of the expressed protein, nucleotides encoding a "signal sequence" may be inserted prior to the cellulase-coding sequence. For expression under the direction of control sequences, a target gene to be treated according to the invention is operably linked to the control sequences in the proper reading frame. Promoter sequences that can be incorporated into plasmid vectors, and which can support the transcription of the mutant cellulase gene, include but are not limited to the prokaryotic β-lactamase promoter (Villa-Kamaroff, et al., 1978, Proc. Natl. Acad. Sci. U.S.A. 75:3727–3731) and the tac promoter (DeBoer, et al., 1983, Proc. Natl. Acad. Sci. U.S.A. 80:21–25). Further references can also be found in "Useful proteins from recombinant bacteria" in Scientific American, 1980, 242:74–94.

According to one embodiment B. subtilis is transformed by an expression vector carrying the mutated DNA. If expression is to take place in a secreting microorganism such as B. subtilis a signal sequence may follow the translation initiation signal and precede the DNA sequence of interest. The signal sequence acts to transport the expression product to the cell wall where it is cleaved from the product upon secretion. The term "control sequences" as defined above is intended to include a signal sequence, when is present.

In a currently preferred method of producing cellulase variants of the invention, a filamentous fungus is used as the host organism. The filamentous fungus host organism may conveniently be one which has previously been used as a host for producing recombinant proteins, e.g. a strain of Aspergillus sp., such as A. niger, A. nidulans or A. oryzae. The use of A. oryzae in the production of recombinant proteins is extensively described in, e.g. EP 238 023.

For expression of cellulase variants in Aspergillus, the DNA sequence coding for the cellulase variant is preceded by a promoter. The promoter may be any DNA sequence exhibiting a strong transcriptional activity in Aspergillus and may be derived from a gene encoding an extracellular or intracellular protein such as an amylase, a glucoamylase, a protease, a lipase, a cellulase or a glycolytic enzyme.

Examples of suitable promoters are those derived from the gene encoding A. oryzae TAKA amylase, Rhizomucor miehei aspartic proteinase, A. niger neutral α-amylase, A. niger acid stable α-amylase, A. niger glucoamylase, Rhizomucor miehei lipase, A. oryzae alkaline protease or A. oryzae triose phosphate isomerase.

In particular when the host organism is A. oryzae, a preferred promoter for use in the process of the present invention is the A. oryzae TAKA amylase promoter as it exhibits a strong transcriptional activity in A. oryzae. The sequence of the TAKA amylase promoter appears from EP 238 023.

Termination and polyadenylation sequences may suitably be derived from the same sources as the promoter.

The techniques used to transform a fungal host cell may suitably be as described in EP 238 023.

To ensure secretion of the cellulase variant from the host cell, the DNA sequence encoding the cellulase variant may be preceded by a signal sequence which may be a naturally occurring signal sequence or a functional part thereof or a synthetic sequence providing secretion of the protein from the cell. In particular, the signal sequence may be derived from a gene encoding an Aspergillus sp. amylase or glucoamylase, a gene encoding a Rhizomucor miehei lipase or protease, or a gene encoding a Humicola cellulase, xylanase or lipase. The signal sequence is preferably derived from the gene encoding A. oryzae TAKA amylase, A. niger neutral α-amylase, A. niger acid-stable α-amylase or A. niger glucoamylase.

The medium used to culture the transformed host cells may be any conventional medium suitable for growing Aspergillus cells. The transformants are usually stable and may be cultured in the absence of selection pressure. However, if the transformants are found to be unstable, a selection marker introduced into the cells may be used for selection.

The mature cellulase protein secreted from the host cells may conveniently be recovered from the culture medium by well-known procedures including separating the cells from the medium by centrifugation or filtration, and precipitating proteinaceous components of the medium by means of a salt such as ammonium sulphate, followed by chromatographic procedures such as ion exchange chromatography, affinity chromatography, or the like.

For example, the endoglucanase of the present invention was produced by Aspergillus oryzae after transformation with a plasmid containing the disclosed sequence and using the normal taka promotor and AMG terminator. The fermentation broth was purified by filtration and concentration using ultrafiltration. See also example 4.

Hybridization conditions (to be used in evaluating property ii) of the cloned DNA sequence of the invention)

Suitable conditions for determining hybridization between a nucleotide probe and a homologous DNA or RNA sequence involves presoaking of the filter containing the DNA fragments or RNA to hybridize in 5×SSC (standard saline citrate) for 10 min, and prehybridization of the filter in a solution of 5×SSC (Sambrook et al. 1989), 5× Denhardt's solution (Sambrook et al. 1989), 0.5% SDS and 100 μg/ml of denatured sonicated salmon sperm DNA (Sambrook et al. 1989), followed by hybridization in the same solution containing a random-primed (Feinberg, A. P. and Vogelstein, B. (1983) Anal. Biochem. 132:6–13), $^{32}$P-dCTP-labeled (specific activity>1×10$^9$ cpm/μg) probe for 12 hours at ca. 45° C. The filter is then washed two times for 30 minutes in 2×SSC, 0.5% SDS at preferably not higher than 50° C., more preferably not higher than 55° C., more preferably not higher than 60° C., more preferably not higher than 65° C., even more preferably not higher than 70° C., especially not higher than 75° C.

The nucleotide probe to be used in the hybridization is the DNA sequence corresponding to the endoglucanase encoding part of the DNA sequence shown in SEQ ID No. 2.

Immunological cross-reactivity

Antibodies to be used in determining immunological cross-reactivity may be prepared by use of a purified cellulase. More specifically, antiserum against the cellulase of the invention may be raised by immunizing rabbits (or other rodents) according to the procedure described by N. Axelsen et al. in: *A Manual of Quantitative Immunoelectrophoresis,* Blackwell Scientific Publications, 1973, Chapter 23, or A. Johnstone and R. Thorpe, *Immunochemistry in Practice,* Blackwell Scientific Publications, 1982 (more specifically pp. 27–31). Purified immunoglobulins may be obtained from the antisera, for example by salt precipitation $((NH_4)_2SO_4)$, followed by dialysis and ion exchange chromatography, e.g. on DEAE-Sephadex. Immunochemical characterization of proteins may be done either by Outcherlony double-diffusion analysis (O. Outcherlony in: *Handbook of Experimental Immunology* (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2).

Detergent Compositions

According to the invention, the cellulase of the invention or an endoglucanase derived from a strain of *Humicola insolens* and having the amino acid sequence listed in SEQ ID NO:1 and an apparent molecular weight of about 50 kD measured in SDS-PAGE may typically be a component of a detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molar weights of 1000 to 20000, ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% water and 0–30% organic solvent, or nonaqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0–40% of nonionic surfactant such as alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as amylase, lipase, cutinase, protease, other cellulases, peroxidase, and oxidase, e.g., laccase).

The detergent may contain 1–65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose (CMC), poly (vinylpyrrolidone) (PVP), polyethyleneglycol (PEG), poly (vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) or nonanoyloxybenzenesulfonate (NOBS). Alternatively, the bleaching system may comprise peroxyacids of, e.g., the amide, imide, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative such as, e.g., an aromatic borate ester, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil-redeposition agents, dyes, bactericides, optical brighteners, or perfume.

The pH (measured in aqueous solution at use concentration) will usually be neutral or alkaline, e.g. in the range of 7–11.

Particular forms of detergent compositions within the scope of the invention include:

1) A detergent composition formulated as a granulate having a bulk density of at least 600 g/l comprising

| | |
|---|---|
| Linear alkylbenzenesulfonate (calculated as acid) | 7–12% |
| Alcohol ethoxysulfate (e.g., $C_{12-18}$ alcohol, 1–2 EO) or alkyl sulfate (e.g., $C_{16-18}$) | 1–4% |
| Alcohol ethoxylate (e.g., $C_{14-15}$ alcohol, 7 EO) | 5–9% |
| Sodium carbonate (as $Na_2CO_3$) | 14–20% |
| Soluble silicate (as $Na_2O, 2SiO_2$) | 2–6% |
| Zeolite (as $NaAlSiO_4$) | 15–22% |
| Sodium sulfate (as $Na_2SO_4$) | 0–6% |
| Sodium citrate/citric acid (as $C_6H_5Na_3O_7/C_6H_8O_7$) | 0–15% |
| Sodium perborate (as $NaBO_3 \cdot H_2O$) | 11–18% |
| TAED | 2–6% |
| Carboxymethylcellulose | 0–2% |
| Polymers (e.g., maleic/acrylic acid copolymer, PVP, PEG) | 0–3% |
| Enzymes (calculated as pure enzyme protein) | 0.0001–0.1% |
| Minor ingredients (e.g., suds suppressors, perfume, optical brightener, photobleach) | 0–5% |

2) A detergent composition formulated as a granulate having a bulk density of at least 600 g/l comprising

| | |
|---|---|
| Linear alkylbenzenesulfonate (calculated as acid) | 6–11% |
| Alcohol ethoxysulfate (e.g., $C_{12-18}$ alcohol, 1–2 EO or alkyl sulfate (e.g., $C_{16-18}$) | 1–3% |
| Alcohol ethoxylate (e.g., $C_{14-15}$ alcohol, 7 EO) | 5–9% |
| Sodium carbonate (as $Na_2CO_3$) | 15–21% |
| Soluble silicate (as $Na_2O, 2SiO_2$) | 1–4% |
| Zeolite (as $NaAlSiO_4$) | 24–34% |
| Sodium sulfate (as $Na_2SO_4$) | 4–10% |
| Sodium citrate/citric acid (as $C_6H_5Na_3O_7/C_6H_8O_7$) | 0–15% |

-continued

| | |
|---|---|
| Carboxymethylcellulose | 0–2% |
| Polymers (e.g., maleic/acrylic acid copolymer, PVP, PEG) | 1–6% |
| Enzymes (calculated as pure enzyme protein) | 0.0001–0.1% |
| Minor ingredients (e.g., suds suppressors, perfume) | 0–5% |

3) A detergent composition formulated as a granulate having a bulk density of at least 600 g/l comprising

| | |
|---|---|
| Linear alkylbenzenesulfonate (calculated as acid) | 5–9% |
| Alcohol ethoxylate (e.g., $C_{12-15}$ alcohol, 7 EO) | 7–14% |
| Soap as fatty acid (e.g., $C_{16-22}$ fatty acid) | 1–3% |
| Sodium carbonate (as $Na_2CO_3$) | 10–17% |
| Soluble silicate (as $Na_2O, 2SiO_2$) | 3–9% |
| Zeolite (as $NaAlSiO_4$) | 23–33% |
| Sodium sulfate (as Na2SO4) | 0–4% |
| Sodium perborate (as $NaBO_3.H_2O$) | 8–16% |
| TAED | 2–8% |
| Phosphonate (e.g., EDTMPA) | 0–1% |
| Carboxymethylcellulose | 0–2% |
| Polymers (e.g., maleic/acrylic acid copolymer, PVP, PEG) | 0–3% |
| Enzymes (calculated as pure enzyme protein) | 0.0001–0.1% |
| Minor ingredients (e.g., suds suppressors, perfume, optical brightener) | 0–5% |

4) A detergent composition formulated as a granulate having a bulk density of at least 600 g/l comprising

| | |
|---|---|
| Linear alkylbenzenesulfonate (calculated as acid) | 8–12% |
| Alcohol ethoxylate (e.g., $C_{12-15}$ alcohol, 7 EO) | 10–25% |
| Sodium carbonate (as $Na_2CO_3$) | 14–22% |
| Soluble silicate (as $Na_2O, 2SiO_2$) | 1–5% |
| Zeolite (as $NaAlSiO_4$) | 25–35% |
| Sodium sulfate (as $Na_2SO_4$) | 0–10% |
| Carboxymethylcellulose | 0–2% |
| Polymers (e.g., maleic/acrylic acid copolymer, PVP, PEG) | 1–3% |
| Enzymes (calculated as pure enzyme protein) | 0.0001–0.1% |
| Minor ingredients (e.g., suds suppressors, perfume) | 0–5% |

5) An aqueous liquid detergent composition comprising

| | |
|---|---|
| Linear alkylbenzenesulfonate (calculated as acid) | 15–21% |
| Alcohol ethoxylate (e.g., $C_{12-15}$ alcohol, 7 EO or $C_{12-15}$ alcohol, 5 EO) | 12–18% |
| Soap as fatty acid (e.g., oleic acid) | 3–13% |
| Alkenylsuccinic acid ($C_{12-14}$) | 0–13% |
| Aminoethanol | 8–18% |
| Citric acid | 2–8% |
| Phosphonate | 0–3% |
| Polymers (e.g., PVP, PEG) | 0–3% |
| Borate (as $B_4O_7$) | 0–2% |
| Ethanol | 0–3% |
| Propylene glycol | 8–14% |
| Enzymes (calculated as pure enzyme protein) | 0.0001–0.1% |
| Minor ingredients (e.g., dispersants, suds suppressors, perfume, optical brightener) | 0–5% |

6) An aqueous structured liquid detergent composition comprising

| | |
|---|---|
| Linear alkylbenzenesulfonate (calculated as acid) | 15–21% |
| Alcohol ethoxylate (e.g., $C_{12-15}$ alcohol, 7 EO, or $C_{12-15}$ alcohol, EO) | 3–9% |
| Soap as fatty acid (e.g., oleic acid) | 3–10% |
| Zeolite (as $NaAlSiO_4$) | 14–22% |
| Potassium citrate | 9–18% |
| Borate (as $B_4O_7$) | 0–2% |
| Carboxymethylcellulose | 0–2% |
| Polymers (e.g., PEG, PVP) | 0–3% |
| Anchoring polymers such as, e.g., lauryl methacrylate/acrylic acid copolymer; molar ratio 25:1; MW 3800 | 0–3% |
| Glycerol | 0–5% |
| Enzymes (calculated as pure enzyme protein) | 0.0001–0.1% |
| Minor ingredients (e.g., dispersants, suds suppressors, perfume, optical brighteners) | 0–5% |

7) A detergent composition formulated as a granulate having a bulk density of at least 600 g/l comprising

| | |
|---|---|
| Fatty alcohol sulfate | 5–10% |
| Ethoxylated fatty acid monoethanolamide | 3–9% |
| Soap as fatty acid | 0–3% |
| Sodium carbonate (as $Na_2CO_3$) | 5–10% |
| Soluble silicate (as $Na_2O, 2SiO_2$) | 1–4% |
| Zeolite (as $NaAlSiO_4$) | 20–40% |
| Sodium sulfate (as $Na_2SO_4$) | 2–8% |
| Sodium perborate (as $NaBO_3.H_2O$) | 12–18% |
| TAED | 2–7% |
| Polymers (e.g., maleic/acrylic acid copolymer, PEG) | 1–5% |
| Enzymes (calculated as pure enzyme protein) | 0.0001–0.1% |
| Minor ingredients (e.g., optical brightener, suds suppressors, perfume) | 0–5% |

8) A detergent composition formulated as a granulate comprising

| | |
|---|---|
| Linear alkylbenzenesulfonate (calculated as acid) | 8–14% |
| Ethoxylated fatty acid monoethanolamide | 5–11% |
| Soap as fatty acid | 0–3% |
| Sodium carbonate (as $Na_2CO_3$) | 4–10% |
| Soluble silicate (as $Na_2O, 2SiO_2$) | 1–4% |
| Zeolite (as $NaAlSiO_4$) | 30–50% |
| Sodium sulfate (as $Na_2SO_4$) | 3–11% |
| Sodium citrate (as $C_6H_5Na_3O_7$) | 5–12% |
| Polymers (e.g., PVP, maleic/acrylic acid copolymer, PEG) | 1–5% |
| Enzymes (calculated as pure enzyme protein) | 0.0001–0.1% |
| Minor ingredients (e.g., suds suppressors, perfume) | 0–5% |

9) A detergent composition formulated as a granulate comprising

| | |
|---|---|
| Linear alkylbenzenesulfonate (calculated as acid) | 6–12% |
| Nonionic surfactant | 1–4% |
| Soap as fatty acid | 2–6% |
| Sodium carbonate (as $Na_2CO_3$) | 14–22% |
| Zeolite (as $NaAlSiO_4$) | 18–32% |
| Sodium sulfate (as $Na_2SO_4$) | 5–20% |
| Sodium citrate (as $C_6H_5Na_3O_7$) | 3–8% |
| Sodium perborate (as $NaBO_3.H_2O$) | 4–9% |
| Bleach activator (e.g., NOBS or TAED) | 1–5% |
| Carboxymethylcellulose | 0–2% |
| Polymers (e.g., polycarboxylate or PEG) | 1–5% |
| Enzymes (calculated as pure enzyme protein) | 0.0001–0.1% |
| Minor ingredients (e.g., optical brightener, perfume) | 0–5% |

10) An aqueous liquid detergent composition comprising

| | |
|---|---|
| Linear alkylbenzenesulfonate (calculated as acid) | 15–23% |
| Alcohol ethoxysulfate (e.g., $C_{12-15}$ alcohol, 2–3 EO) | 8–15% |
| Alcohol ethoxylate (e.g., $C_{12-15}$ alcohol, 7 EO, or $C_{12-15}$ alcohol, 5 EO) | 3–9% |
| Soap as fatty acid (e.g., lauric acid) | 0–3% |
| Aminoethanol | 1–5% |
| Sodium citrate | 5–10% |
| Hydrotrope (e.g., sodium toluensulfonate) | 2–6% |

| | |
|---|---|
| Borate (as B$_4$O$_7$) | 0–2% |
| Carboxymethylcellulose | 0–1% |
| Ethanol | 1–3% |
| Propylene glycol | 2–5% |
| Enzymes (calculated as pure enzyme protein) | 0.0001–0.1% |
| Minor ingredients (e.g., polymers, dispersants, perfume, optical brighteners) | 0–5% |

11) An aqueous liquid detergent composition comprising

| | |
|---|---|
| Linear alkylbenzenesulfonate (calculated as acid) | 20–32% |
| Alcohol ethoxylate (e.g., C$_{12-15}$ alcohol, 7 EO, or C$_{12-15}$ alcohol, 5 EO) | 6–12% |
| Aminoethanol | 2–6% |
| Citric acid | 8–14% |
| Borate (as B$_4$O$_7$) | 1–3% |
| Polymer (e.g., maleic/acrylic acid copolymer, anchoring polymer such as, e.g., lauryl methacrylate/acrylic acid copolymer) | 0–3% |
| Glycerol | 3–8% |
| Enzymes (calculated as pure enzyme protein) | 0.0001–0.1% |
| Minor ingredients (e.g., hydrotropes, dispersants, perfume, optical brighteners) | 0–5% |

12) A detergent composition formulated as a granulate having a bulk density of at least 600 g/l comprising

| | |
|---|---|
| Anionic surfactant (linear alkylbenzenesulfonate, alkyl sulfate, alpha-olefinsulfonate, alpha-sulfo fatty acid methyl esters, alkanesulfonates, soap) | 25–40% |
| Nonionic surfactant (e.g., alcohol ethoxylate) | 1–10% |
| Sodium carbonate (as Na$_2$CO$_3$) | 8–25% |
| Soluble silicates (as Na$_2$O, 2SiO$_2$) | 5–15% |
| Sodium sulfate (as Na$_2$SO$_4$) | 0–5% |
| Zeolite (as NaAlSiO$_4$) | 15–28% |
| Sodium perborate (as NaBO$_3$.4H$_2$O) | 0–20% |
| Bleach activator (TAED or NOBS) | 0–5% |
| Enzymes (calculated as pure enzyme protein) | 0.0001–0.1% |
| Minor ingredients (e.g., perfume, optical brighteners) | 0–3% |

13) Detergent compositions as described in compositions 1–12 wherein all or part of the linear alkylbenzenesulfonate is replaced by (C$_{12}$–C$_{18}$) alkyl sulfate.

14) A detergent composition formulated as a granulate having a bulk density of at least 600 g/l comprising

| | |
|---|---|
| (C$_{12}$–C$_{18}$) alkyl sulfate | 9–15% |
| Alcohol ethoxylate | 3–6% |
| Polyhydroxy alkyl fatty acid amide | 1–5% |
| Zeolite (as NaAlSiO$_4$) | 10–20% |
| Layered disilicate (e.g., SK56 from Hoechst) | 10–20% |
| Sodium carbonate (as Na$_2$CO$_3$) | 3–12% |
| Soluble silicate (as Na$_2$O, 2SiO$_2$) | 0–6% |
| Sodium citrate | 4–8% |
| Sodium percarbonate | 13–22% |
| TAED | 3–8% |
| Polymers (e.g., polycarboxylates and PVP) | 0–5% |
| Enzymes (calculated as pure enzyme protein) | 0.0001–0.1% |
| Minor ingredients (e.g., optical brightener, photo bleach, perfume, suds suppressors) | 0–5% |

15) A detergent composition formulated as a granulate having a bulk density of at least 600 g/l comprising

| | |
|---|---|
| (C$_{12}$—C$_{18}$) alkyl sulfate | 4–8% |
| Alcohol ethoxylate | 11–15% |
| Soap | 1–4% |
| Zeolite MAP or zeolite A | 35–45% |
| Sodium carbonate (as Na$_2$CO$_3$) | 2–8% |
| Soluble silicate (as Na$_2$O, 2SiO$_2$) | 0–4% |
| Sodium percarbonate | 13–22% |
| TAED | 1–8% |
| Carboxymethyl cellulose | 0–3% |
| Polymers (e.g., polycarboxylates and PVP) | 0–3% |
| Enzymes (calculated as pure enzyme protein) | 0.0001–0.1% |
| Minor ingredients (e.g., optical brightener, phosphonate, perfume) | 0–3% |

16) Detergent compositions as described in compositions 1–15 which contain a stabilized or encapsulated peracid, either as an additional component or as a substitute for already specified bleach systems.

17) Detergent compositions as described in compositions 1, 3, 7, 9 and 12 wherein perborate is replaced by percarbonate.

18) Detergent compositions as described in compositions 1, 3, 7, 9, 12, 14 and 15 which additionally contain a manganese catalyst. The manganese catalyst may, e.g., be one of the compounds described in "Efficient manganese catalysts for low-temperature bleaching", 1994, Nature 369:637–639.

19) Detergent composition formulated as a nonaqueous detergent liquid comprising a liquid nonionic surfactant such as, e.g., linear alkoxylated primary alcohol, a builder system (e.g., phosphate), enzyme and alkali. The detergent may also comprise anionic surfactant and/or a bleach system.

The endoglucanase of the invention may be incorporated in concentrations conventionally employed in detergents. It is at present contemplated that, in the detergent composition of the invention, the endoglucanase may be added in an amount corresponding to 0.00001–1 mg (calculated as pure enzyme protein) of endoglucanase per liter of wash liquor.

In yet another aspect, the present endoglucanases may be used in fabric softeners, e.g. as described in Surfactant and Consumer Products, Ed. by J. Falbe, 1987, pp 295–296; Tenside Surfactants Detergents, 30 (1993), 6, pp 394–399; JAOCS, Vol. 61 (1984), 2, pp 367–376; EP 517 762; EP 123 400; WO 92/19714; WO 93/19147; U.S. Pat. No. 5,082,578; EP 494 769; EP 544 493; EP 543 562; U.S. Pat. No. 5,235,082; EP 568 297; EP 570 237.

The present invention also relates to a washing process wherein soiled fabric is treated with a cellulase of the invention or an endoglucanase derived from a strain of Humicola insolens and having the amino acid sequence listed in SEQ ID NO:3 and an apparent molecular weight of about 50 kD measured in SDS-PAGE.

It is contemplated that, dependent on the specificity of the modified cellulase, it may be employed for one or possibly more of the applications mentioned above, i.e. in the baking industry, in the wine and juice industry, for animal feed, and in textile and papermaking pulp processing. In a particular embodiment, the enzyme preparation of the invention may comprise a combination of one or more modified cellulases with enzymes selected from the group consisting of unmodified or modified amylases, lipases, proteases, oxidoreductases and hemicellulases.

Pulp and paper applications

In the papermaking pulp industry, the cellulase and/or enzyme preparation according to the invention may be applied advantageously e.g. as follows:

For debarking: pretreatment with the cellulase and/or enzyme preparation according to the invention may degrade the cambium layer prior to debarking in mechanical drums resulting in advantageous energy savings.

For defibration: treatment of a material containing cellulosic fibers with the cellulase and/or enzyme preparation of the invention prior to refining or beating may result in reduction of the energy consumption due to the hydrolysing effect of the cellulase on the interfiber surfaces. Use of the cellulase and/or enzyme preparation of the invention may result in improved energy savings as compared to the use of unmodified enzymes, since it is believed that the modified cellulase may possess a higher ability to penetrate fiber walls.

For fiber modification, i.e. improvement of fiber properties where partial hydrolysis across the fiber wall is needed which requires deeper penetrating enzymes (e.g. in order to make coarse fibers more flexible). Deep treatment of fibers has so far not been possible for high yield pulps e.g. mechanical pulps or mixtures of recycled pulps. This has been ascribed to the nature of the fiber wall structure that prevents the passage of enzyme molecules due to physical restriction of the pore matrix of the fiber wall. It is contemplated that the modified (i.e. derivatised) cellulases of the invention are capable of penetrating into the fiber wall.

For drainage improvement. The drainability of papermaking pulps may be improved by treatment of the pulp with hydrolysing enzymes, e.g. cellulases. Use of the modified cellulase and/or enzyme preparation according to the invention may be more effective, e.g. result in a higher degree of loosening bundles of strongly hydrated micro-fibrils in the fines fraction (consisting of fiber debris) that limits the rate of drainage by blocking hollow spaces between fibers and in the wire mesh of the paper machine. The Canadian standard freeness (CSF) increases and the Schopper-Riegler drainage index decreases when pulp in subjected to cellulase treatment, see e.g. U.S. Pat. No. 4,923,565; TAPPI T227, SCAN C19:65 which are hereby incorporated by reference.

For inter fiber bonding. Hydrolytic enzymes are applied in the manufacture of papermaking pulps for improving the inter fiber bonding. The enzymes rinse the fiber surfaces for impurities e.g. cellulosic debris, thus enhancing the area of exposed cellulose with attachment to the fiber wall, thus improving the fiber-to-fiber hydrogen binding capacity. This process is also referred to as dehornification. Paper and board produced with a cellulase containing enzyme preparation according to the invention may have an improved strength or a reduced grammage, a smoother surface and an improved printability. These improvements are believed to be a result of the improved penetrability of the modified/derivatised enzyme(s).

For enzymatic deinking. Partial hydrolysis of recycled paper during or upon pulping by use of hydrolysing enzymes such as cellulases are known to facilitate the removal and agglomeration of ink particles. Use of a modified cellulase and/or enzyme preparation according to the invention may give a more effective loosening of ink from the surface structure due to a better penetration of the enzyme molecules into the fibrillar matrix of the fiber wall, thus softening the surface whereby ink particles are effectively loosened. The agglomeration of loosened ink particles are also improved, due to a more efficient hydrolysis of cellulosic fragments found attached to ink particles originating from the fibers.

The treatment of lignocellulosic pulp may, e.g., be performed as described in WO 91/14819, WO 91/14822, WO 92/17573 and WO 92/18688.

Textile applications

In another embodiment, the present invention relates to use of the modified cellulase and/or enzyme preparation according to the invention in the bio-polishing process. Bio-Polishing is a specific treatment of the yarn surface which improves fabric quality with respect to handle and appearance without loss of fabric wettability. The most important effects of Bio-Polishing can be characterized by less fuzz and pilling, increased gloss/luster, improved fabric handle, increased durable softness and altered water absorbency. Bio-Polishing usually takes place in the wet processing of the manufacture of knitted and woven fabrics. Wet processing comprises such steps as e.g. desizing, scouring, bleaching, washing, dyeing/printing and finishing. During each of these steps, the fabric is more or less subjected to mechanical action. In general, after the textiles have been knitted or woven, the fabric proceeds to a desizing stage, followed by a scouring stage, etc. Desizing is the act of removing size from textiles. Prior to weaving on mechanical looms, warp yarns are often coated with size starch or starch derivatives in order to increase their tensile strength. After weaving, the size coating must be removed before further processing the fabric in order to ensure a homogeneous and wash-proof result. It is known that in order to achieve the effects of Bio-Polishing, a combination of cellulolytic and mechanical action is required. It is also known that "super-softness" is achievable when the treatment with cellulase is combined with a conventional treatment with softening agents. It is contemplated that use of the modified cellulase and/or enzyme preparation of the invention for bio-polishing of cellulosic fabrics is advantageous, e.g. a more thorough polishing can be achieved. Bio-polishing may be obtained by applying the method described e.g. in WO 93/20278.

Degradation of plant material

In yet another embodiment, the present invention relates to use of a modified cellulase and/or enzyme preparation according to the invention for degradation of plant material e.g. cell walls.

It is contemplated that the modified cellulase and/or enzyme preparation of the invention is useful in the preparation of wine, fruit or vegetable juice in order to increase yield. Cellulases according to the invention may also be applied for enzymatic hydrolysis of various plant cell-wall derived materials or waste materials, e.g. agricultural residues such as wheat-straw, corn cobs, whole corn plants, nut shells, grass, vegetable hulls, bean hulls, spent grains, sugar beet pulp, and the like. The plant material may be degraded in order to improve different kinds of processing, facilitate purification or extraction of other components like purification of beta-glucan or beta-glucan oligomers from cereals, improve the feed value, decrease the water binding capacity, improve the degradability in waste water plants, improve the conversion of e.g. grass and corn to ensilage, etc.

In a preferred embodiment of the invention, the cellulase is an endoglucanase. The cellulolytic activity of endoglucanase is determined relative to an analytical standard and may be expressed in the unit ECU.

Determination of cellulolytic activity

Cellulolytic enzymes hydrolyse CMC, thereby decreasing the viscosity of the incubation mixture. The resulting reduction in viscosity may be determined by a vibration viscosimeter (e.g. MIVI 3000 from Sofraser, France).

Determination of the cellulolytic activity, measured in terms of ECU, may be determined according to the analysis method AF 301.1 which is available from the Applicant upon request.

The ECU assay quantifies the amount of catalytic activity present in the sample by measuring the ability of the sample to reduce the viscosity of a solution of carboxymethylcellulose (CMC). The assay is carried out at 40° C., pH 7.5 using a relative enzyme standard for reducing the viscosity of the CMC substrate.

Cellulase activity on cellotriose

The cellulase activity on cellotriose, in terms of $k_{cat} \cdot s^{-1}$, was determined by a coupled assay:

| | | |
|---|---|---|
| Cellotriose | → Glucose + Cellobiose | (cat.: cellulase) |
| Glucose + $O_2$ + $H_2O$ | → Gluconate + $H_2O_2$ | (cat.: Glucoseoxidase) |
| $H_2O_2$ + $ABTS^R$ | → $ABTS^{Ox}$ | (cat.: Peroxidase) | which is followed spectrophotometrically at 418 nm (maximum absorbance of $ABTS^{Ox}$ at 418 nm).

Method

The GOD-Perid Test Kit (available from Boehringer Mannheim, art. 124 036) was used. The buffer-enzyme solution in the test kit was dissolved in 500 ml milli Q water. pH of the solution was adjusted to 8.5 (NaOH).

80 mg of $ABTS^R$ (available from Boehringer Mannheim, art. 756 407) was dissolved in 10 ml GOD-Perid corresponding to a total concentration of $ABTS^R$ of 10 mg/ml.

A substrate stock solution of 5 mmole (2.52 mg/ml) of cellotriose (available from Merck art. 24741) in water was prepared. Diluted solutions in water corresponding to 1000 μmole, 500 μmole, 376 μmole, 250 μmole, 100 μmole and 60 μmole were prepared.

The reaction mixture was prepared by mixing 1 part of substrate solution with 1 part of GOD-Perid.

A solution of the cellulase enzyme to be determined in a concentration of 1.0–3.0 μmole was prepared.

50 μl of enzyme solution and 450 μl of reaction mixture were mixed.

The measurements were carried out on a HP 8452A Diode Array Spectrophotometer thermostated at 40° C., 1 cm cuvette, at a wavelength of 418 nm. The reaction was followed by measuring the oxidation af ABTS every 20 sec for 600 sec in total.

Calculations

The cellulase activity on cellotriose, in terms of $k_{cat} \cdot s^{-1}$, was calculated from a Lineweaver-Burk plot (a plot of 1/V versus 1/[S]): the slope and the intersection were determined by linear regression analysis.

The following constants were used for the calculations:

Cellulase: $\epsilon = 66,310 \, M^{-1} \cdot cm^1$ $ABTS^{Ox}$: $\epsilon = 0.0323 \, \mu mole^{-1} \cdot cm^{-1}$ For EG I' from *Fusarium oxysporum*, the catalytic activity on cellotriose at pH 8.5 and 40° C. was calculated to 5.5 $K_{cat}$ pr. sec. $K_m$ was 0.5 mM.

Determination of alkaline cellulase activity on amorphous cellulose

Method

Substrate preparation 20 gram acid-swollen AVICEL® stock solution (see below for a preparation which can be stored for one month) was centrifuged for 20 min. at 5000 rpm., the supernatant was poured off, and the sediment was resuspended in 30 ml of buffer. Then centrifuged for 20 min. at 5000 rpm, the supernatant was poured off, and the sediment was resuspended in buffer to a total of 30 g. This corresponds to a substrate concentration of 10 g AVICEL/liter.

Buffer 0.1M Barbital at pH 8.5 or 0.1M Glycine at pH 10.0

Enzyme solution

The enzymes were diluted to an activity of 0.5 S-CEVU/ml at pH 8.5 or 0.75 S-CEVU/ml at pH 10.0.

Reagents

2% NaOH, PHBAH-reagent: 1.5 g of p-hydroxy benzoic acid hydrazide and 5.0 g sodium tartrate was dissolved in 100 ml of 2% NaOH.

The substrate, the buffer and the enzyme solution were mixed as follows:

| Substrate (μl) | Buffer (μl) | Enzyme sol. (μl) | Subst. conc. (final) (g/l) |
|---|---|---|---|
| 50 | 1950 | 500 | 0.20 |
| 125 | 1875 | 500 | 0.50 |
| 250 | 1750 | 500 | 1.00 |
| 500 | 1500 | 500 | 2.00 |
| 750 | 1250 | 500 | 3.00 |
| 1000 | 1000 | 500 | 4.00 |

The substrate/buffer solution was preheated for 5 min at 40° C. Then the enzyme solution was added and the solution was whirlmixed for 5 sec., followed by incubation for 20 min. at 40° C.

The reaction was stopped by adding 500 μl 2% NaOH solution, followed by whirlmixing for 5 sec.

The samples were centrifuged for 20 min. at 5000 rpm.

1000 μl of supernatant was transferred from the test tubes to new test tubes, and 500 μl PHBAH-reagent was added, followed by boiling for 10 min.

The test tubes were cooled in ice water.

The absorbance of the samples were measured on a spectrophotometer at 410 nm.

Standard glucose curve

A stock solution containing 300 mg/l was diluted to 5, 10, 15 and 25 mg/l.

1000 μl of the diluted standards were mixed with 500 μl of PHBAH-reagent, and were treated as the other samples, see above.

Determination of activity

The release of reducing glucose equivalent was calculated using the standard curve.

The enzyme concentration was calculated using the molar absorbance of 66310 ($\epsilon$) for the EG I endoglucanase. The $K_m$, $V_{max}$ and $K_{cat}$ was calculated from a Lineweaver-Burk plot using different substrate concentrations.

The molar absorbance of the cellulase variants having substituted tyrosines and tryptophanes was adjusted accordingly using a absorbance value for tryptophane of 5690($\epsilon$) and for tyrosine of 1280($\epsilon$) and cystein 120($\epsilon$).

The extinction coefficients ($\epsilon$) are disclosed in Gill, S. C. and Hippel, P. H.: Calculation of protein extinction coefficients from amino acid sequence data; Analytical Biochemistry vol 182, (319–326), (1989).

Each of the tested cellulases was purified to high homogeneity giving a single band in SDS-PAGE analysis (the ratio $A_{280}/A_{260}$ was checked as being above 1.5).

Preparation of Acid swollen cellulose

Materials 5 g Avicel®. (Art. 2331 Merck)

150 ml 85% Ortho-phosphoric-acid. (Art. 573 Merck)

400 ml Acetone. (Art. 14 Merck)

1.3 l Deionized water (Milli Q)

1 l glass beaker 1 l glass filter funnel 2 l suction flask

Ultra Turrax Homogenizer

Procedure

The Acetone and the phosphoric-acid was cooled on ice.

The 5 g. Avicel® was moistened with water, then 150 ml of ice cold 85% Orthophosphoric-acid was added, and the mixture was placed on ice bath with weak stirring for 1 h.

100 ml of ice cold acetone was added with stirring, followed by transfer of the mixture to a glass filter funnel, followed by washing with 3×100 ml ice cold acetone and dry suction after each washing.

The filter cake was washed with 2×500 ml water and sucked as dry as possible after each wash. The filter cake was resuspended to a total volume of 300 ml and blended to homogeneity (using the Ultra Turrax Homogenizer). The resulting product was stored in a refrigerator.

The following result was obtained:

EG I* from *Humicola insolens*:

$k_{cat}$ at 8.5: 16 per sec $k_{cat}$ at 10: 12 per sec

The extinction coefficient was 66310.

EGI-Fus from *Fusarium oxysporum*:

$k_{cat}$ at 8.5, 40° C.: 16 per sec (km 8 g/l)

$k_{cat}$ at 10, 40° C.: 4 per sec ($k_m$ 8 g/l)

The molar extinction coefficient was 58180, calculated based on the amino acid composition.

EXAMPLE 1

Multi cycle terg-o-tometer test EG I* versus EG I

The example illustrates the superior soil removal effects of EG I* (truncated EG I, 402 amino acids) versus EG I (415 amino acids, WO 91/17244 FIGS. 14A–E). In the example EMPA 101 swatches have been used as soil removal tracers (carbon black/olive oil).

The following detergent composition was used:

|  | % by weight |
|---|---|
| LAS, (Nansa 1169/p) | 10.3 |
| AES, (Berol 452) | 3.5 |
| SOAP (C18) | 0.5 |
| SOAP (C14) | 0.5 |
| AEO (Dobanol 25-7) | 6.4 |
| Sodiumxylenesulfonat | 5.1 |
| Ethanol | 0.7 |
| MPG | 2.7 |
| Glycerol | 0.5 |
| Sodium sulphate | 0.40 |
| Sodium carbonate | 2.7 |
| Sodium citrate | 4.4 |
| Citric acid | 1.5 |
| Water | Rest |

Testing procedure

The test was based on a 2 cycle wash test in a terg-o-tometer using the detergent composition described above in a 0.3% solution with 1 mM Ca++.

Agitation: 150 m/min

Temperature: 40° C.

pH: 8.2

Swatches: EMPA 101 (2 swatches á 5×6 cm pr 100 ml)

Washing time: 20 minutes

Rinse: 10 minutes in tapwater

Drying: Line drying at room temperature

Repetitions: 2

Result

The soil removal result is given as Delta remmision R (Enzyme-treated versus blind) measured at 420 nm with an Elrepho apparatus (DataColor).

| Enzyme | R (S.D.) Delta R |
|---|---|
| No enzyme | 41.99 (0.41) 0 |
| EG I, 4 ECU/1 | 42.00 (0.28) 0.01 |
| EG I, 8 ECU/1 | 41.24 (0.45) −0.75 |
| EG I, 12 ECU/1 | 42.69 (0.32) 0.71 |
| EG I, 20 ECU/1 | 43.05 (0.32) 1.06 |

EXAMPLE 2

Carbon dispersing effect of EG I*

The particulate soil removing effect of endoglucanases is expected partly to be ascribed to the cleavage of glycosidic bonds in the cellulose matrix, but to some extent the enzyme may also provide a more non-specific cleaning effect, for instance, by improving the dispersability of the particulate soil.

In this test it is shown that EG I* (truncated EG I, 402 amino acids) differs from EG I (415 amino acids, WO 91/17244 FIGS. 14A–E) with respect to its ability to disperse active carbon.

Different amounts of purified EG I and EG I* were added into 10 ml of a 1 g/l suspension of active carbon (Norit) in 10 mM Phosphate buffer, pH 10.

The mixtures were incubated for 30 minutes at 55° C. and 150 rpm.

After incubation the samples were allowed to cool to ambient temperature and non-dispersed carbon was allowed to settle (no centrifugation) for 15 minutes. The amount of carbon that was dispersed was evaluated by measuring the $OD_{582\ nm}$ of the supernatant (at 582 nm was found a peak maximum most likely resulting from scattering). Due to the nature of the experiment (inhomogeneous solutions, time dependence etc), the absolute $OD_{582\ nm}$ levels may vary among the tests carried out, whereas the relative levels usually may be conserved.

The table below show the results obtained in the test:

| Enzyme | Conc.(mg/l) | ΔOD(582 nm) |
|---|---|---|
| EG I | 5 | 0.09 |
|  | 10 | 0.30 |
| EG I* | 5 | 0.40 |
|  | 10 | 0.49 |

ΔOD(582 nm) = $OD_{582\ nm}$(with enxzyme)-$OD_{582\ nm}$(without enzyme)

$OD_{582\ nm}$(without enzyme) = 0.716

The results show that EG I* differs significantly from EG I in terms of its carbon dispersion ability—at 5 mg/l level the ΔOD(582 nm) obtained with EG I* is four times as high as that obtained with EG I. Also it should be noted that the effect of EG I* is actually very large—the apparant level of detergency is increased by about 70% in the presence of 10 mg/l EG I*.

EXAMPLE 3

Tensile strength loss induced by cellulase

Cellulases used for soil removal in detergents often gives rise to an increased fabric wear. This can be observed through a reduced tensile strength of the fabric.

In the present example three cellulases are compared: Celluzyme® (a known commercial cellulase preparation), EG I* from *H. insolens* and EG I-Fus from Fusarium.

Celluzyme® is a multicomplex cellulase product from *Humicola insolens* used in detergents for soil removal and color clarification.

Experimental

Buffer: 0.05 M Tris-HCl, pH 7.0, 1 mM CaCl₂

Textile/cup: 4 pcs. á 5×25 cm; woven fabric (app. 18 g)

Dosage:

10000 ECU/l of Celluzyme®, *Humicola insolens* EGI PPC 4192, Fusarium EGI-161294/MChr.

Volume: 100 ml

Time: 7 days dark storage, 25° C.

Rinse: 10 min in deionized water.

Evaluation: Tensile strength is measured as wet pull on Instron.

The following results were obtained:

|  | % tensile strength loss |
|---|---|
| Blind (no cellulase) | 0% ± 8% **) |
| Celluzyme | 41% |
| *H. insolens* EG I* | 8% |
| Fusarium EGI-Fus | −4% |

**) 0% pr. definition; 8% is relative standard deviation.

From the results it can be concluded that EG I* from *H. insolens* and EGI-Fus from *Fusarium oxysporum* are effective for soil removal but their use do not result in significant tensile strength loss in textile fabric.

EXAMPLE 4

Purification and characterization of an Endoglucanase I cloned from *Myceliophthora thermophila*

The endoglucanase I cloned from the strain *Myceliophthora thermophila* and encoded by the DNA sequence shown in SEQ ID NO:2 was purified and characterized.

The clone was purified an anion-exchange Mono Q column:

Column: Mono Q® Pharmacia column

Buffer A: 50 mmol Tris pH 7.0

Buffer B: 50 mmol Tris+0.5 M NaCl pH 7.0

Flow: 1 ml/min

Gradient: 30 min 0%–100% buffer B.

The active fractions were pooled and the following results were obtained.

Results

MW 50 kD pI 3.5

Km and Kcat was determined on cellotriose as described above at pH 7.5 to:

Km: 368 mmol

Kcat: 5.48 s−1

Km and Kcat was determined on acid swollen cellulose as described above at pH 8.5 and 10:

| pH 8.5 | Km: 22 mmol |
|---|---|
|  | Kcat: 15 s-1 |
| pH 10 | Km: 42 mmol |
|  | Kcat: 3.5 s-1 |

Further, it was determined that the endoglucanase exhibited cellulolytic active in a pH range from about 3 to about 9.5. The optimum catalytic activity of the enzyme was found to be at a temperature of about 50–55° C.

We claim:

1. An isolated core cellulase derived from a strain of *Myceliophthora thermophila* encoded by an amino acid sequence selected from the group consisting of:
   (a) amino acids 21–420 of SEQ ID NO:1; or
   (b) a sequence at least 95% homologous with the sequence of (a).

2. The core cellulase of claim 1, further comprising amino acids 1–20 of SEQ ID NO:1.

3. The core cellulase of claim 2, further comprising amino acids 421–456 of SEQ ID NO:1.

4. The cellulase of claim 2 which further comprises a C-terminal link consisting of up to 10 amino acids.

5. A detergent composition comprising a cellulase according to claim 1 and a surfactant.

6. A detergent composition according to claim 5, which further comprises one or more other enzymes selected from the group consisting of amylases, lipases, proteases, cellulases, peroxidases and oxidases.

7. A process for washing a soiled fabric, comprising treating the soiled fabric with a cellulase according to claim 1.

8. A method for preventing backstaining in washing of fabric and bio-polishing of textiles, comprising treating fabric with the cellulase of claim 1.

* * * * *